US008846058B2

(12) United States Patent
Smith et al.

(10) Patent No.: US 8,846,058 B2
(45) Date of Patent: Sep. 30, 2014

(54) SHIGA TOXOID CHIMERIC PROTEINS

(75) Inventors: Michael J. Smith, Silver Spring, MD (US); Alison D. O'Brien, Bethesda, MD (US); Louise D. Teel, Silver Spring, MD (US); Angela R. Melton-Celsa, Sterling, VA (US)

(73) Assignee: The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 565 days.

(21) Appl. No.: 12/279,423

(22) PCT Filed: Feb. 16, 2007

(86) PCT No.: PCT/US2007/004513
§ 371 (c)(1),
(2), (4) Date: Jan. 12, 2009

(87) PCT Pub. No.: WO2007/098201
PCT Pub. Date: Aug. 30, 2007

(65) Prior Publication Data
US 2009/0226469 A1    Sep. 10, 2009

Related U.S. Application Data

(60) Provisional application No. 60/773,658, filed on Feb. 16, 2006.

(51) Int. Cl.
*A61K 39/02* (2006.01)
*C07K 14/245* (2006.01)
*A61K 39/108* (2006.01)
*C12N 15/62* (2006.01)
*A61K 39/00* (2006.01)

(52) U.S. Cl.
CPC .............. *C12N 15/62* (2013.01); *C07K 14/245* (2013.01); *A61K 2039/55566* (2013.01); *A61K 39/0258* (2013.01); *C07K 2319/55* (2013.01); *A61K 39/00* (2013.01)
USPC .................. 424/236.1; 424/185.1; 424/192.1; 424/241.1

(58) Field of Classification Search
USPC ....................... 424/185.1, 192.1, 236.1, 241.1
See application file for complete search history.

(56) References Cited

U.S. PATENT DOCUMENTS 5,552,144 A * 9/1996 Samuel et al. ............. 424/236.1

FOREIGN PATENT DOCUMENTS

WO     WO 98/011229     3/1998

OTHER PUBLICATIONS

Accession #P69179; P08027 (UniProtKB/Swiss-Prot, 1988).*

Houghten et al. New Approaches to Immunization, Vaccines 86, Cold Spring Harbor Laboratory, p. 21-25, 1986.*
Accession #Q8XBV2 (UniprotKB/TrEMBL, 2002).*
Wen et al. Vaccine 24 (2006) 1142-1148.*
Smith et al. Vaccine 24 (2006) 4122-4129.*
Di et al. Toxicon (2011), doi:10.1016/j.toxicon.2010.12.006.*
Greenspan et al (Nature Biotechnology 7: 936-937, 1999).*
Chothia et al (The EMBO Journal, 1986, 5/4:823-26.*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Andreoli et al. "Hemolytic uremic syndrome: epidemiology, pathophysiology, and therapy", Pediatr. Nephrol., 17, 293-8 (2002).
Bielaszewska et al. "Localization of intravenously administered verocytotoxins (Shiga-like toxins) 1 and 2 . . . ", Infect. Immun., 65, 2509-16 (1997).
Calderwood et al. "Nucleotide sequence of the Shiga-like toxin genes of *Escherichia coli*", Proc. Natl. Acad. Sci. USA, 84(13), 4364-8 (1987).
Deresiewicz et al. "Mutations affecting the activity of the Shiga-like toxin I A-chain", Biochemistry, 31(12), 3272-80 (1992).
Deresiewicz et al. "The role of tyrosine-114 in the enzymatic activity of the Shiga-like toxin I A-chain", Mol. Gen. Genet., 241(3-4), 467-73 (1993).
Fraser et al. "Crystal structure of the holotoxin from *Shigella dysenteriae* at 2.5 A resolution", Nat. Struct. Biol., 1, 59-64 (1994).
Fraser et al. "Structure of shiga toxin type 2 (Stx2) from *Escherichia coli* O157:H7", J. Biol. Chem., 279, 27511-7 (2004).
Gordon et al. "An enzymatic mutant of Shiga-like toxin II variant is a vaccine candidate for edema disease of swine", Infect. Immun., 60, 485-90 (1992).
Head et al. "Preparation of VT1 and VT2 hybrid toxins from their purified dissociated subunits. Evidence for B subunit . . .", J. Biol. Chem., 266, 3617-3621 (1991).
Hovde et al. "Evidence that glutamic acid 167 is an active-site residue of Shiga-like toxin I", Proc. Natl. Acad. Sci. USA, 85(8), 2568-72 (1988).

(Continued)

*Primary Examiner* — Jennifer Graser
(74) *Attorney, Agent, or Firm* — Morgan, Lewis & Bockius LLP

(57) ABSTRACT

A chimeric Shiga toxoid according to the invention contains an enzymatically-inactivated StxA subunit and a native StxB subunit. This hybrid Shiga toxoid induces the production of broadly cross-reactive species of antibodies against Shiga toxin following immunization. The StxA subunit is modified so that it is enzymatically inactive. The invention thus encompasses the Shiga toxoid or fragments thereof and the nucleic acid sequence of the Shiga toxoid or fragments thereof. The invention further encompasses the production of a Shiga toxoid, the production of antibodies using the Shiga toxoid and methods of productions, and an immunogenic composition containing the Shiga toxoid.

12 Claims, 3 Drawing Sheets

(56) References Cited

OTHER PUBLICATIONS

Ishikawa et al. "Protection against Shiga toxin 1 challenge by immunization of mice with purified mutant Shiga toxin 1", Infect. Immun., 71, 3235-9 (2003).

Jackson et al. "Mutational analysis of the Shiga toxin and Shiga-like toxin II enzymatic subunits", J. Bacteriol., 172(6), 3346-50 (1990).

Klein et al. "Shiga toxin-producing *Escherichia coli* in children with diarrhea: a prospective point-of-care study", J. Pediatr., 141, 172-7 (2002).

Kurohane et al. "Facilitated production of secretory IgA against Shiga toxin B subunits by intranasal application . . . ", Microbiol Immunol., 49(2), 149-54 (2005).

Lindgren et al. "The specific activities of Shiga-like toxin type II (SLT-II) and SLT-II-related toxins . . . ", Infect. Immun., 62, 623-31 (1994).

Lindgren et al. "Virulence of enterohemorrhagic *Escherichia coli* O91:H21 clinical isolates in an orally infected mouse model", Infect. Immun., 61, 3832-42 (1993).

Ludwig et al. "Cross-protection against challenge by intravenous *Escherichia coli* verocytotoxin 1 (VT1) in rabbits. . . ", Can. J. Microbiol., 48, 99-103 (2002).

Marcato et al. "Immunoprophylactic potential of cloned Shiga toxin 2 B subunit", J. Infect. Dis., 183(3), 435-43 (2001).

Mead et al. "Food-related illness and death in the United States", Emerg. Infect. Dis., 5, 607-25 (1999).

Melton-Celsa et al. "Activation of Shiga toxin type 2d (Stx2d) by elastase involves cleavage of the C-terminal two amino acids . . . ", Molecular Microbiology, 43, 207-215 (2002).

Yamaski et al. "Importance of arginine at position 170 of the A subunit of Vero toxin 1 produced by enterohemorrhagic . . . ", Microb Pathog., 11(1), 1-9 (1991).

Metz et al. "Physicochemical and immunochemical techniques predict the quality of diphtheria toxoid vaccines", Vaccine, 22, 156-67 (2003).

O'Brien et al. "Shiga-like toxin-converting phages from *Escherichia coli* strains that cause hemorrhagic colitis or infantile diarrhea", Science, 226(4675), 694-6 (1984).

Rangel et al. "Epidemiology of *Escherichia coli* O157:H7 outbreaks, United States, 1982-2002", Emerg. Infect. Dis., 11, 603-9 (2005).

Schmitt et al. "Two copies of Shiga-like toxin II-related genes common in enterohemorrhagic *Escherichia coli* strains . . . ", Infect. Immun., 59, 1065-73 (1991).

Tarr et al. "Shiga-toxin-producing *Escherichia coli* and haemolytic uraemic syndrome", Lancet, 365(9464), 1073-86 (2005).

Wadolkowski et al. "Mouse model for colonization and disease caused by enterohemorrhagic *Escherichia coli* O157:H7", Infect. Immun., 58, 2438-45 (1990).

Weinstein et al. "In vivo formation of hybrid toxins comprising Shiga toxin and the Shiga-like toxins . . . ", Infect. Immun., 57, 3743-50 (1989).

Wen et al. "Genetic toxoids of Shiga toxin types 1 and 2 protect mice against homologous but not heterologous toxin challenge", Vaccine, 24, 1142-8 (2006).

Wong et al. "The risk of the hemolytic-uremic syndrome after antibiotic treatment of *Escherichia coli* O157:H7 infections", N. Engl. J. Med., 342, 1930-6 (2000).

Yamasaki, "Enterohemorrhagic *Escherichia coli* Infection", Nippon Rinsho, Japanese Journal of clinical, 60(6), 1083-8 (2002).

\* cited by examiner

SEQUENCE LISTING

```
<160> NUMBER OF SEQ ID NOS: 25

<210> SEQ ID NO 1
<211> LENGTH: 1442
<212> TYPE: DNA
<213> ORGANISM: Artificial sequence
<220> FEATURE:
<223> OTHER INFORMATION: Chimeric StxA2/StxB1
<220> FEATURE:
<221> NAME/KEY: CDS
<222> LOCATION: (87)..(977)
<220> FEATURE:
<221> NAME/KEY: CDS
<222> LOCATION: (1050)..(1256)

<400> SEQUENCE: 1
ggatcctaag gaggacagct atgaagtgta tattatttaa atgggtactg tgcctgttac     60
tgggtttttc ttcggtatcc tattcc cgg gag ttt acg ata gac ttt tcg acc     113
                             Arg Glu Phe Thr Ile Asp Phe Ser Thr
                             1               5 caa caa agt tat gtc tct tcg tta aat agt ata cgg aca gag ata tcg      161
Gln Gln Ser Tyr Val Ser Ser Leu Asn Ser Ile Arg Thr Glu Ile Ser
10                  15                  20                  25 acc cct ctt gaa cat ata tct cag ggg acc aca tcg gtg tct gtt att      209
Thr Pro Leu Glu His Ile Ser Gln Gly Thr Thr Ser Val Ser Val Ile
                30                  35                  40 aac cac acc cca ccg ggc agt tat ttt gct gtg gat ata cga ggg ctt      257
Asn His Thr Pro Pro Gly Ser Tyr Phe Ala Val Asp Ile Arg Gly Leu
            45                  50                  55 gat gtc tat cag gcg cgt ttt gac cat ctt cgt ctg att att gag caa      305
Asp Val Tyr Gln Ala Arg Phe Asp His Leu Arg Leu Ile Ile Glu Gln
        60                  65                  70 aat aat tta tca gtg gcc ggg ttc gtt aat acg gca aca aat act ttc      353
Asn Asn Leu Ser Val Ala Gly Phe Val Asn Thr Ala Thr Asn Thr Phe
    75                  80                  85 tac cgt ttt tca gat ttt aca cat ata tca gtg ccc ggt gtg aca acg      401
Tyr Arg Phe Ser Asp Phe Thr His Ile Ser Val Pro Gly Val Thr Thr
90                  95                  100                 105 gtt tcc atg aca acg gac agc agt tat acc act ctg caa cgt gtc gca      449
Val Ser Met Thr Thr Asp Ser Ser Tyr Thr Thr Leu Gln Arg Val Ala
                110                 115                 120 gcg ctg gaa cgt tcc gga atg caa atc agt cgt cac tca ctg gtt tca      497
Ala Leu Glu Arg Ser Gly Met Gln Ile Ser Arg His Ser Leu Val Ser
            125                 130                 135 tca tat ctg gcg tta atg gag ttc agt ggt aat aca atg acc aga gat      545
Ser Tyr Leu Ala Leu Met Glu Phe Ser Gly Asn Thr Met Thr Arg Asp
        140                 145                 150 gca tcc aga gca gtt ctg cgt ttt gtc act gtc aca gca caa gcc tta      593
Ala Ser Arg Ala Val Leu Arg Phe Val Thr Val Thr Ala Gln Ala Leu
    155                 160                 165 tta ttc agg cag ata cag aga gaa ttt cgt cag gca ctg tct gaa act      641
Leu Phe Arg Gln Ile Gln Arg Glu Phe Arg Gln Ala Leu Ser Glu Thr
170                 175                 180                 185 gct cct gtg tat acg atg acg ccg gga gac gtg gac ctc act ctg aac      689
Ala Pro Val Tyr Thr Met Thr Pro Gly Asp Val Asp Leu Thr Leu Asn
                190                 195                 200 tgg ggg cga atc agc aat gtg ctt ccg gag tat cgg gga gag gat ggt      737
Trp Gly Arg Ile Ser Asn Val Leu Pro Glu Tyr Arg Gly Glu Asp Gly
            205                 210                 215 gtc aga gtg ggg aga ata tcc ttt aat aat ata tca gcg ata ctg ggg      785
Val Arg Val Gly Arg Ile Ser Phe Asn Asn Ile Ser Ala Ile Leu Gly
        220                 225                 230
```

```
act gtg gcc gtt ata ctg aat tgc cat cat cag ggg gcg cgt tct gtt      833
Thr Val Ala Val Ile Leu Asn Cys His His Gln Gly Ala Arg Ser Val
    235                 240                 245 cgc gcc gtg aat gaa gag agt caa cca gaa tgt cag ata act ggc gac      881
Arg Ala Val Asn Glu Glu Ser Gln Pro Glu Cys Gln Ile Thr Gly Asp
250                 255                 260                 265 agg cct gtt ata aaa ata aac aat aca tta tgg gaa agt aat aca gct      929
Arg Pro Val Ile Lys Ile Asn Asn Thr Leu Trp Glu Ser Asn Thr Ala
                270                 275                 280 gca gcg ttt ctg aac aga aag tca cag ttt tta tat aca acg ggt aaa      977
Ala Ala Phe Leu Asn Arg Lys Ser Gln Phe Leu Tyr Thr Thr Gly Lys
            285                 290                 295 taaggggta aaatgaaaaa aacattatta atagctgcat cgctttcatt tttttcagca    1037
agtgcgctgg cg acg cct gat tgt gta act gga aag gtg gag tat aca aaa   1088
              Thr Pro Asp Cys Val Thr Gly Lys Val Glu Tyr Thr Lys
                  300                 305                 310 tat aat gat gac gat acc ttt aca gtt aaa gtg ggt gat aaa gaa tta     1136
Tyr Asn Asp Asp Asp Thr Phe Thr Val Lys Val Gly Asp Lys Glu Leu
                315                 320                 325 ttt acc aac aga tgg aat ctt cag tct ctt ctt ctc agt gcg caa att     1184
Phe Thr Asn Arg Trp Asn Leu Gln Ser Leu Leu Leu Ser Ala Gln Ile
            330                 335                 340 acg ggg atg act gta acc att aaa act aat gcc tgt cat aat gga ggg     1232
Thr Gly Met Thr Val Thr Ile Lys Thr Asn Ala Cys His Asn Gly Gly
        345                 350                 355 gga ttc agc gaa gtt att ttt cgt tgactcagaa tagctcagtg aaaatagcag    1286
Gly Phe Ser Glu Val Ile Phe Arg
    360                 365 gcggagattc ataatgtta aatacatctc aattcagtca gttgttgccg gtctgataat    1346
agatgtgtta gaaatttct gcatggtgaa tccccctgtg cggaggggcg actggtgaac    1406
ggtatgatct ctttgatgat cgtaagcgag aattcg                             1442

<210> SEQ ID NO 2
<211> LENGTH: 297
<212> TYPE: PRT
<213> ORGANISM: Artificial sequence
<220> FEATURE:
<223> OTHER INFORMATION: Synthetic Construct

<400> SEQUENCE: 2

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Ser Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125
```

```
Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Gln Ala Leu Leu Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg Ala Val Asn Glu Glu Ser
                245                 250                 255

Gln Pro Glu Cys Gln Ile Thr Gly Asp Arg Pro Val Ile Lys Ile Asn
            260                 265                 270

Asn Thr Leu Trp Glu Ser Asn Thr Ala Ala Ala Phe Leu Asn Arg Lys
        275                 280                 285

Ser Gln Phe Leu Tyr Thr Thr Gly Lys
    290                 295
```

```
<210> SEQ ID NO 3
<211> LENGTH: 69
<212> TYPE: PRT
<213> ORGANISM: Artificial sequence
<220> FEATURE:
<223> OTHER INFORMATION: Synthetic Construct

<400> SEQUENCE: 3

Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
            20                  25                  30

Arg Trp Asn Leu Gln Ser Leu Leu Leu Ser Ala Gln Ile Thr Gly Met
        35                  40                  45

Thr Val Thr Ile Lys Thr Asn Ala Cys His Asn Gly Gly Gly Phe Ser
    50                  55                  60

Glu Val Ile Phe Arg
65
```

```
<210> SEQ ID NO 4
<211> LENGTH: 36
<212> TYPE: DNA
<213> ORGANISM: Artificial sequence
<220> FEATURE:
<223> OTHER INFORMATION: Primer

<400> SEQUENCE: 4
gatcggatcc ccctgtaacg aagtttgcgt aacagc                              36
```

```
<210> SEQ ID NO 5
<211> LENGTH: 39
<212> TYPE: DNA
<213> ORGANISM: Artificial sequence
<220> FEATURE:
<223> OTHER INFORMATION: Primer

<400> SEQUENCE: 5
```

```
gatcgaattc tcgcttacga tcatcaaaga gatcatacc                    39
```

<210> SEQ ID NO 6
<211> LENGTH: 38
<212> TYPE: DNA
<213> ORGANISM: Artificial sequence
<220> FEATURE:
<223> OTHER INFORMATION: Primer

<400> SEQUENCE: 6

```
gatcggatcc agcaagggcc accatatcac ataccgcc                     38
```

<210> SEQ ID NO 7
<211> LENGTH: 38
<212> TYPE: DNA
<213> ORGANISM: Artificial sequence
<220> FEATURE:
<223> OTHER INFORMATION: Primer

<400> SEQUENCE: 7

```
cagggaatt caccatgcga aattttttta acaaatgc                      38
```

<210> SEQ ID NO 8
<211> LENGTH: 32
<212> TYPE: DNA
<213> ORGANISM: Artificial sequence
<220> FEATURE:
<223> OTHER INFORMATION: Primer

<400> SEQUENCE: 8

```
gggggtaaaa tgaaaaaaac attattaata gc                           32
```

<210> SEQ ID NO 9
<211> LENGTH: 59
<212> TYPE: DNA
<213> ORGANISM: Artificial sequence
<220> FEATURE:
<223> OTHER INFORMATION: Primer

<400> SEQUENCE: 9

```
gctattaata atgttttttt cattttaccc ccttatttac ccgttgtata taaaaactg   59
```

<210> SEQ ID NO 10
<211> LENGTH: 25
<212> TYPE: DNA
<213> ORGANISM: Artificial sequence
<220> FEATURE:
<223> OTHER INFORMATION: Primer

<400> SEQUENCE: 10

```
tcagtggccg ggttcgttaa tacgg                                   25
```

<210> SEQ ID NO 11
<211> LENGTH: 61
<212> TYPE: DNA
<213> ORGANISM: Artificial sequence
<220> FEATURE:
<223> OTHER INFORMATION: Primer

<400> SEQUENCE: 11

```
ccgtattaac gaacccggcc actgataaat tattttgctc aataatcaga cgaagatggt   60
c                                                             61
```

<210> SEQ ID NO 12

<211> LENGTH: 44
<212> TYPE: DNA
<213> ORGANISM: Artificial sequence
<220> FEATURE:
<223> OTHER INFORMATION: Primer

<400> SEQUENCE: 12
caagccttat tattcaggca gatacagaga gaatttcgtc aggc                                         44

<210> SEQ ID NO 13
<211> LENGTH: 64
<212> TYPE: DNA
<213> ORGANISM: Artificial sequence
<220> FEATURE:
<223> OTHER INFORMATION: Primer

<400> SEQUENCE: 13
ctctgtatct gcctgaataa taaggcttgt gctgtgacag tgacaaaacg cagaactgct            60
ctgg                                                                        64

<210> SEQ ID NO 14
<211> LENGTH: 54
<212> TYPE: DNA
<213> ORGANISM: Artificial sequence
<220> FEATURE:
<223> OTHER INFORMATION: Primer

<400> SEQUENCE: 14
gatcggatcc taaggaggac agctatgaag tgtatattat ttaaatgggt actg                  54

<210> SEQ ID NO 15
<211> LENGTH: 34
<212> TYPE: DNA
<213> ORGANISM: Artificial sequence
<220> FEATURE:
<223> OTHER INFORMATION: Primer

<400> SEQUENCE: 15
gatcatcgat agccaaaagg aacacctgta tatg                                        34

<210> SEQ ID NO 16
<211> LENGTH: 37
<212> TYPE: DNA
<213> ORGANISM: Artificial sequence
<220> FEATURE:
<223> OTHER INFORMATION: Primer

<400> SEQUENCE: 16
gatcgctagc tcaacgaaaa ataacttcgc tgaatcc                                     37

<210> SEQ ID NO 17
<211> LENGTH: 21
<212> TYPE: DNA
<213> ORGANISM: Artificial sequence
<220> FEATURE:
<223> OTHER INFORMATION: Primer

<400> SEQUENCE: 17
caggccttat tattcaggca g                                                      21

<210> SEQ ID NO 18
<211> LENGTH: 60
<212> TYPE: DNA
<213> ORGANISM: Artificial sequence
<220> FEATURE:
<223> OTHER INFORMATION: Primer

<400> SEQUENCE: 18
ctgcctgaat aataaggcct gtgctgtgac agtgacaaaa cgcagaactg ctctggatgc    60

<210> SEQ ID NO 19
<211> LENGTH: 34
<212> TYPE: DNA
<213> ORGANISM: Artificial sequence
<220> FEATURE:
<223> OTHER INFORMATION: Primer

<400> SEQUENCE: 19
ggtggtggtg acgaaaaata acttcgctga atcc                                34

<210> SEQ ID NO 20
<211> LENGTH: 32
<212> TYPE: DNA
<213> ORGANISM: Artificial sequence
<220> FEATURE:
<223> OTHER INFORMATION: Primer

<400> SEQUENCE: 20
cagtggtggt ggtggtggtg acgaaaaata ac                                  32

<210> SEQ ID NO 21
<211> LENGTH: 31
<212> TYPE: DNA
<213> ORGANISM: Artificial sequence
<220> FEATURE:
<223> OTHER INFORMATION: Primer

<400> SEQUENCE: 21
gatcgaattc tcagtggtgg tggtggtggt g                                   31

<210> SEQ ID NO 22
<211> LENGTH: 29
<212> TYPE: DNA
<213> ORGANISM: Artificial sequence
<220> FEATURE:
<223> OTHER INFORMATION: Primer

<400> SEQUENCE: 22
catcacgata cctttacagt taaagtggg                                      29

<210> SEQ ID NO 23
<211> LENGTH: 46
<212> TYPE: DNA
<213> ORGANISM: Artificial sequence
<220> FEATURE:
<223> OTHER INFORMATION: Primer

<400> SEQUENCE: 23
tttaactgta aaggtatcgt gatgattata ttttgtatac tccacc                   46

<210> SEQ ID NO 24
<211> LENGTH: 17
<212> TYPE: DNA
<213> ORGANISM: Artificial sequence
<220> FEATURE:
<223> OTHER INFORMATION: Shine-Dalgarno sequence

<400> SEQUENCE: 24
taaggaggac agctatg                                                   17

<210> SEQ ID NO 25

```
<211> LENGTH: 297
<212> TYPE: PRT
<213> ORGANISM: Enterobacteria phage 933W

<400> SEQUENCE: 25

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg Ala Val Asn Glu Glu Ser
                245                 250                 255

Gln Pro Glu Cys Gln Ile Thr Gly Asp Arg Pro Val Ile Lys Ile Asn
            260                 265                 270

Asn Thr Leu Trp Glu Ser Asn Thr Ala Ala Ala Phe Leu Asn Arg Lys
        275                 280                 285

Ser Gln Phe Leu Tyr Thr Thr Gly Lys
    290                 295
```

SHIGA TOXOID CHIMERIC PROTEINS

RELATED APPLICATION

The present application is a U.S. National Phase application of International Application PCT/US2007/004513, filed Feb. 16, 2007, which claims the benefit of U.S. Provisional Application 60/773,658, filed Feb. 16, 2006, which is incorporated by reference in its entirety.

ACKNOWLEDGMENT OF FEDERAL SUPPORT

This present invention arose in part from research funded by federal grant NIH AI20148-23.

REFERENCE TO SEQUENCE LISTING

The application includes a text file of a computer readable version of the sequence listing, entitled "044508-5015-US-SubSequenceListing.txt" and having a size of about 16 kb, which has been submitted on 23 Nov. 2011 herewith and is incorporated by reference.

FIELD OF THE INVENTION

The present invention relates to a chimeric Shiga toxoid, which can be used to vaccinate against Shiga toxins.

BACKGROUND OF THE INVENTION

In the United States, Shiga toxin (Stx)-producing *Escherichia coli* (STEC) are the most common cause of infectious bloody diarrhea (Rangel et al. (2005) Emerg. Infect. Dis. 11, 603-9) and account for about 110,000 infections per year (Mead et al. (1999) Emerg. Infect. Dis. 5, 607-25). The majority of Stx-mediated disease is attributable to a subset of STEC, the enterohemorrhagic *E. coli*, which include the prototypic serotype O157:H7. The hemolytic uremic syndrome (HUS) is a serious sequela of STEC (particularly O157:H7) infection that is characterized by hemolytic anemia, thrombic thrombocytopenia and renal failure, especially amongst the most vulnerable patients—children and the elderly. The fatality rate in those who experience HUS is five to ten percent, with the potential for residual kidney and neurological damage among survivors. Therapy for STEC-infections includes supportive care, rehydration and kidney dialysis (Andreoli et al. (2002) Pediatr. Nephrol. 17, 293-8; Klein et al. (2002) J. Pediatr. 141, 172-7; and Tarr et al. (2005) Lancet 365(9464), 1073-86). No interventional therapy or vaccine is currently available. Furthermore, antibiotic treatment is contraindicated due to the increased risk of HUS (Wong et al. (2000) N. Engl. J. Med. 342, 1930-6) that may result from induction of the lytic cycle of the toxin-converting phages that encode Stxs in *E. coli*.

There are two main types of Stxs. Members of the first type, Stx produced by *S. dysenteriae* type 1 and Stx1 produced by *E. coli* are virtually identical. The second type, Stx2 is also encoded by *E. coli*; however, it is not cross-neutralized by polyclonal antisera against Stx1, or vice versa (O'Brien et al. (1984) Science 226(4675), 694-6). Variants of each Stx serogroup exist (e.g., Stx1c, Stx1d, Stx2c, Stx2d, Stx2d-activatable, Stx2e, Stx2f) (Melton-Celsa et al. (2005) EcoSal-*Escherichia coli* and *Salmonella*: Cellular and Molecular Biology, ASM Press, Chapter 8.7.8) but they remain neutralizable by polyclonal sera to the prototype toxin (Schmitt et al. (1991) Infect Immun 59, 1065-73; Lindgren et al. (1994) Infect. Immun. 62, 623-31). Stxs are complex holotoxins with an AB5 composition. They have an enzymatically active (A) subunit and a binding domain (B) composed of five identical B proteins of about 7.7 kDa each that form a pentamer. The A subunit is a ~32 kDa protein that is asymmetrically cleaved by trypsin or furin into the A1 subunit (about 27 kDa) and the A2 peptide (about 5 kDa) that remain associated through a disulfide bond. The mature A and B subunits of Stx1 and Stx2 have 55% and 61% identity and 68% and 73% similarity, respectively. Despite the amino acid sequence differences, the crystal structures of the holotoxins are remarkably similar (Fraser et al. (1994) Nat. Struct. Biol. 1, 59-64; Fraser et al. (2004) J. Biol. Chem. 279, 27511-7) and the toxins have the same mode of action. The A1 subunit contains the enzymatically active region, an N-glycosidase that removes an adenosine residue from the 28S rRNA from the 60S ribosome. This alteration halts protein synthesis and kills the intoxicated cell. The A2 peptide traverses the B pentamer to tether the holotoxin together non-covalently. The B pentamer binds the eukaryotic receptor globotriaosyl ceramide (Gb3) or Gb4, as is the case for Stx2e.

Efforts to develop vaccines protective against both Stx types have thus far been frustrating. Stxs are extremely potent and inactivation of the enzymatic activity is necessary to utilize the holotoxins as vaccines. One alternative is to use the B subunits to elicit antibodies that block binding of the B pentamer to the GB3 cellular receptor. This approach has been successful with StxB1 to raise protection against Stx1 challenge, but immununization with the StxB2 subunit is ineffective in protecting against Stx2. Furthermore, passive immunization of mice with anti-StxA2 monoclonal antibody protects mice from the effects of infection with Stx2-producing strains while anti-StxB1 monoclonal antibody is not protective against such a challenge (Wadolkowski et al. (1990) Infect. Immun. 58, 2438-45; Lindgren et al. (1993) Infect. Immun. 61, 383242). However, mice injected with an otherwise lethal dose of Stx1 or Stx2 are protected by passive immunization with anti-StxB1 or anti-StxA2, respectively. The toxicity of the StxA subunits is greatly abrogated without the B pentamer binding domain and there is evidence that vaccines composed of StxA1 and StxA2 offer homologous toxin protection in rabbits (Bielaszewska et al. (1997) Infect. Immun. 65, 2509-16). However, for safety, inactivation of enzymatic activity would be necessary for use of an A subunit vaccine in humans. Subunit vaccines in general are less desirable from the perspective that holotoxin is likely to provide a broader spectrum of protective antibodies than a subunit vaccine.

Protection against toxin-mediated diseases by immunization with toxoid (inactivated holotoxin) vaccines is successful for tetanus and diphtheria. Unfortunately, chemical inactivation of Stxs with formaldehyde or gluteraldehyde is an ill-defined chemical process that can result in residual toxicity (Metz et al. (2003) Vaccine 22, 156-67; Gordon et al. (1992) Infect. Immun. 60, 485-90) or potential distortion of the native holotoxin structure such that neutralizing antibodies are not generated or are of low titer. Some reports in the literature suggest that cross-neutralization has been achieved in animals vaccinated with chemically prepared Shiga toxoids (Bielaszewska et al. (1997) Infect. Immun. 65, 2509-16; Ludwig et al. (2002) Can. J. Microbiol. 48, 99-103); however, the potential for life-threatening toxicity of such a vaccine precludes the use of chemical Stx toxoids in humans. A safer alternative to chemically derived Stx toxoids is the construction of genetic toxoids through the introduction of specific mutations in the Stx A subunit genes to change key amino acids of the enzymatically active domain. Hybrid Stx1 and Stx2 toxins have been made for functional studies of Stxs (Head et al. (1991) J. Biol. Chem. 266, 3617-3621; Weinstein et al. (1989) Infect. Immun. 57, 3743-50; Melton-Celsa et al. (2002) Molecular Microbiology 43, 207-215), including operon fusions allowing A and B subunit expression as a single operon (Weinstein et al., supra). Genetic toxoids of Stx1 or Stx2 that protect animals from subsequent lethal challenges of either Stx1 or Stx2 have previously been made (Gordon et al. (1992) Infect. Immun. 60, 485-90; Ishikawa et al. (2003) Infect. Immun. 71, 3235-9; Wen et al. (2006) Vaccine 24, 1142-8). However, such genetic toxoids are unable to circumvent the lack of cross-neutralization between the Stx1 and Stx2 serogroups and only protect against the Stx group from which they were made. To date, there has been no report in the literature of Stx hybrid toxoids being generated.

SUMMARY OF THE INVENTION

The invention encompasses a chimeric protein comprising at least one StxA polypeptide or a fragment thereof with one or more modifications at one or more active sites, and at least one StxB polypeptide. In some embodiments, the chimeric protein exists as a pentamer. In further embodiments, the StxB polypeptide or fragment thereof comprises one or more modifications wherein the one or more modifications is an amino acid substitution, addition and/or deletion. In some embodiments, the substitution is a conservative amino acid substitution. In further embodiments, the StxA polypeptide is StxA2 or a fragment thereof and/or the StxB polypeptide is StxB1 or a fragment thereof. In another embodiment, the protein comprises or consists of the amino acid sequence of SEQ ID NO: 2 and/or 3.

In further embodiments, the chimeric proteins of the invention comprise one or more modifications at an amino acid residue in the Stx2A polypeptide or fragment thereof corresponding to residue 77, 167 or 170. In some embodiments, the modification at residue 77 is the substitution of a serine residue while the modification at residue 167 is the substitution of a glutamine, asparagine or other amino acid residue and the modification at residue 170 is the substitution of a leucine residue. In some embodiments, the modification is capable of reducing or eliminating the enzymatic activity of the Stx2A polypeptide as described herein. In some embodiments, the modification is capable of reducing or eliminating the enzymatic activity of the Stx2A polypeptide as described herein. In other embodiments, the modifications render the protein non-toxic to mammals.

The invention also encompasses an isolated antibody that binds to the chimeric toxoid proteins of the invention and as described herein. In some embodiments, the antibody is a polyclonal antibody. The invention also encompasses a composition comprising one or more of any of the chimeric toxoid proteins of the invention as described herein. In some embodiments, the chimeric protein is capable of inducing an immunogenic response, including, but not limited to, an immunogenic response to Shiga toxin. In some embodiments, the composition further comprises one or more pharmaceutically acceptable carrier(s) and/or adjuvant(s). In another embodiment, the composition is suitable for administration to a human.

The invention further encompasses an isolated nucleic acid molecule that encodes the chimeric toxoid proteins of the invention as described herein. In some embodiments, the isolated nucleic acid molecule encodes an amino acid sequence comprising SEQ ID NO: 2 and/or 3. In additional embodiments, the nucleic acid molecule comprises or consists of the nucleotide sequence of SEQ ID NO: 1. In some embodiments, the nucleotide sequence exhibits at least 90%, 95% or even up to 99% sequence identity with the contiguous nucleotide sequence of SEQ ID NO: 1 and encodes a polypeptide which is capable of inducing an immunogenic response to Stx.

The invention also encompasses a host cell transformed to contain the nucleic acids of the invention as described herein and includes a vector comprising the isolated nucleic acids. The invention also includes a host cell comprising the aforementioned vector. In some embodiments, the host is selected from the group consisting of prokaryotic and eukaryotic hosts. The invention further encompasses a method of producing a polypeptide comprising culturing a host cell transformed with the nucleic acid molecule of the invention under conditions in which the protein encoded by the nucleic acid molecule is expressed.

The invention includes a method of generating antibodies capable of binding to Stx comprising administering a chimeric toxoid protein of the invention as described herein to a mammal or cell culture. The invention further includes a method of generating antibodies capable of binding to Stx comprising administering the composition comprising the chimeric toxoid proteins of the invention to a mammal. In some embodiments, the mammal is a human. In additional embodiments, the human is suffering from diarrhea and/or hemolytic uremic syndrome.

The invention also encompasses a method of preventing hemolytic uremic syndrome in a human comprising administering a composition comprising the chimeric toxoid proteins of the invention. The invention encompasses a method of preventing diarrhea associated with Shiga toxin-producing *Escherichia coli* infection in a human comprising administering the aforementioned composition. The invention also includes an isolated antibody produced by the any of these methods and a kit comprising this antibody. In some embodiments, the kit further comprises one or more chimeric toxoid proteins of the invention.

DETAILED DESCRIPTION

Figure 1:
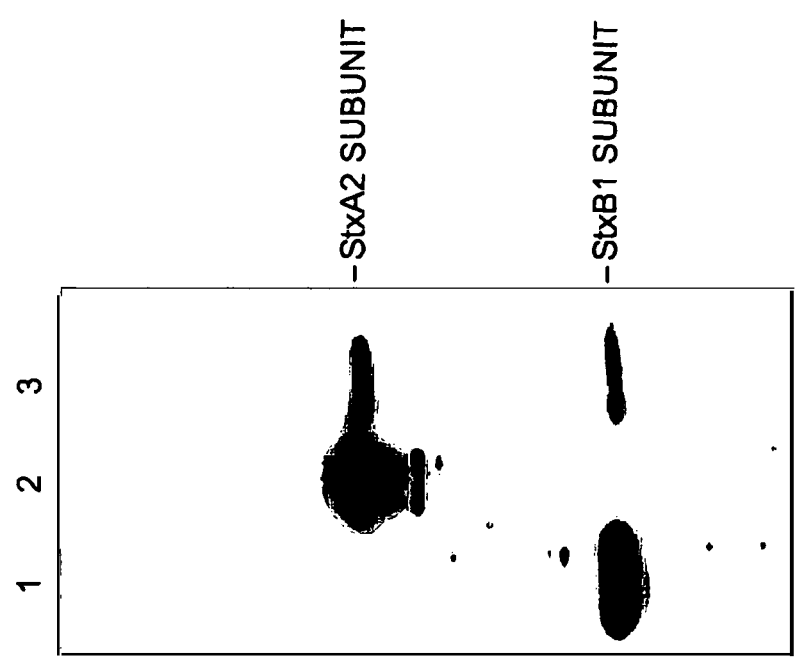
FIG. 1: Western blot analysis of chimeric StxA2/StxB1 toxoid. Wild-type Stx1, Stx2 and chimeric StxA2/StxB1 toxoid (300 ng each) were separated on a 15% SDS-polyacrylamide gel and probed with monoclonal antibody (MAb) hybridoma supernatants directed against StxB1 and StxA2 (13C4 and 11E10 MAbs, respectively). Lane 1 contains Stx1, lane 2 contains Stx2 and lane 3 contains the StxA2/StxB1 toxoid.

A goal of immunization against Stx and hemolytic uremic syndrome (HUS) is to induce neutralizing antibody responses (NA) broadly reactive against multiple types of Stxs including but not limited to, Stx 1 and 2, and variants of Stx1 and Stx2. The present inventors have studied Stx-producing *E. coli* (STEC) and determined that creation of a chimeric Shiga toxoid with modifications at one or more sites in this hybrid toxoid induces the production of broadly cross-reactive species of antibodies against Stx following immunization. The invention therefore encompasses chimeric Shiga toxoids, methods of use, and compositions. As used herein, "toxoid" refers to an inactivated holotoxin. As used herein, "enzymatically-inactivated StxA2 subunit" refers to a StxA2 subunit that has lost its functionality through mutations such as e.g., substitutions, additions, and/or deletions.

Shiga Toxoid Chimeric Proteins and Method of Use

The invention encompasses a chimeric Shiga toxoid protein that contains an enzymatically-inactivated StxA2 subunit and the native StxB1 subunit. The StxA2 subunit is inactivated at one or more sites either singly or in combination by site-directed mutagenesis. In some embodiments, the amino acids are deleted while in some embodiments, the amino acids are substituted. Notwithstanding the deletion(s) and/or substitution(s), the conformation of the StxA2 subunit remains sufficiently intact to induce antibodies to multiple subunits of Stxs following administration to a mammal. Mammals, including but not limited to, humans, and/or mice that are immunized with this modified chimeric toxoid develop an immune response, which will reduce or block HUS or other effects of STEC infection or Stx intoxication.

Exemplary suitable substitution sites in the StxA2 protein include, but are not limited to amino acids in StxA2 corresponding to residues 77, 167 and 170 of SEQ ID NO: 2. The substitutions may be Y77S, E167Q and R170L or equivalents. In one embodiment of the invention, the invention encompasses amino acid sequences as set forth in SEQ ID NO: 2 and 3 and fragments thereof. In another embodiment of the invention, the invention encompasses a chimeric Shiga toxoid that contains an enzymatically-inactivated StxA2 subunit and the native StxB1 subunit of the amino acid sequences as set forth in SEQ ID NO: 2 and/or 3 and fragments thereof.

In some embodiments of the invention, the StxB1 subunit does not bind to, or has limited binding to the GB3 receptor but is capable of evoking a protective antibody response.

The invention includes chimeric and/or fusion polypeptides and salts thereof, comprising at least one Shiga toxoid protein and at least one second polypeptide. In some embodiments, the second polypeptide includes a second type of Stx.

The second polypeptide can also include a stabilization domain, which increases the in vitro and in vivo half-life of the fusion polypeptide. As used herein, the term "stabilization domain" refers to an amino acid sequence capable of extending the in vitro and in vivo half-life of a Shiga toxoid when compared to the Shiga toxoid alone. The stabilization domain can comprise human proteins (e.g., full length or truncated, soluble proteins from extracellular fragments, etc) such as human serum albumin, transferrin, or other proteins, which stabilize the in vivo or in vitro half-life of the chimeric toxoid protein. These additional functional domains may themselves serve as linker peptides, for example, for joining a Shiga toxoid to a second protein. Alternatively, they may be located elsewhere in the fusion molecule (e.g., at the amino or carboxy terminus thereof). In alternative embodiments, the stabilization domain is a chemical moiety (e.g., PEG (polyethylene glycol) or a dextran).

The term "chimeric" or "fusion polypeptide" as used herein refers to polypeptides in which: (i) a given functional domain (i.e. a Shiga toxoid) is bound at its carboxy terminus by a non-covalent bond either to the amino terminus of a second protein (i.e., a second Shiga toxoid) or to a linker peptide which itself is bound by a non-covalent bond to the amino terminus of the second protein; (ii) a given functional domain (i.e. a Shiga toxoid) is bound at its amino terminus by a non-covalent bond either to the carboxy terminus of a second protein (i.e., a second Shiga toxoid) or to a linker peptide which itself is bound by a non-covalent bond to the carboxy terminus of the second protein; and/or (iii) the Stxs exist as complex holotoxins with an AB5 composition as described herein and having an enzymatically active (A) subunit and a binding domain (B) composed of five identical B proteins that form a pentamer.

Similarly, "fused" when used in connection with the nucleic acid intermediates of the invention means that the 3'- [or 5'-] terminus of a nucleotide sequence encoding a protein is bound to the respective 3'- [or 5'-] terminus of a nucleotide sequence encoding a second protein, either by a covalent bond or indirectly via a nucleotide linker which itself is covalently bound preferably at its termini to the first functional domain-encoding polynucleotide and optionally, a second functional domain-encoding nucleic acid.

Examples of chimeric or fusion polypeptides of the invention may be represented by, but are not limited by, the following formulas:

R1-L-R2                                                   (i)

R2-L-R1                                                  (ii)

R1-L-R2-L-R1                                     (iii)

R1-L-R1-L-R2                                     (iv)

R2-L-R1-L-R1                                     (iv)

wherein R1 is the amino acid sequence of a first Shiga toxoid, R2 is the amino acid sequence of a second Shiga toxoid or a stabilizing domain (e.g., human serum albumin), each L is a linker peptide which is bound by a covalent bond to a terminus of R1 and/or R2, whereby the above molecule fragments are read directionally (i.e., with the left side corresponding to the amino terminus and the right side to the carboxy terminus of the molecule). In another embodiment, all or part of an intimin protein (Carvalho et al. (2005) Infect. Immun. 73, 2541-2546), that includes the intimin binding domain (carboxy terminus), is R1 and R2 is the chimeric toxoid protein.

Nucleic Acid Molecules and Methods of Use

The present invention further provides nucleic acid molecules that encode the chimeric Shiga toxoid proteins of the invention including a chimeric protein with an enzymatically-inactivated StxA2 subunit and the native StxB1 subunit or fragments thereof, preferably in isolated form. As used herein, "nucleic acid" is defined as RNA or DNA that encodes a protein or peptide as defined above, is complementary to a nucleic acid sequence encoding such peptides, hybridizes to nucleic acid molecules that encode an enzymatically-inactivated StxA2 subunit and the native StxB1 subunit across the open reading frame under appropriate stringency conditions or encodes a polypeptide that shares at least about 65% identity with inactivated StxA2 and about 91% identity with StxB1, alternatively at least about 90% identity with inactivated StxA2 and about 91% identity with StxB1, alternatively at least about 99% identity with inactivated StxA2 and about 95% identity with StxB1, alternatively at least 99.4% identity with inactivated StxA2 and about 99% identity with StxB1.

The nucleic acids of the invention further include nucleic acid molecules that share at least about 90%, alternatively at least about 95%, alternatively at least about 98%, alternatively at least about 99% or more identity with the contiguous nucleotide sequence of nucleic acid molecules that encode the chimeric Shiga toxoid that contains an enzymatically-inactivated StxA2 subunit and the native StxB1 subunit including SEQ ID NO: 2 and/or 3.

In some embodiments of the invention, the nucleic acid molecules contain double or triple base substitutions in the coding region for the StxA2 gene in codons encoding suitable substitution sites such as e.g., in the codons encoding amino acid residues 77, 167 and 170 of the StxA2 protein (SEQ ID NO: 2).

In another embodiment, the nucleic acid molecules contain modifications (e.g., substitutions, additions, and/or deletions) in the coding region for the StxB1 gene that prevent the StxB1 protein from interacting with the kidney cells (via e.g. the host cell GB3 receptor). In one embodiment, such a modification is in one or more codons encoding amino acid residues 16 and/or 17 of the StxB1 protein. These modifications may give rise to amino acid substitutions of D16H and D17H or equivalents. In another embodiment, such a modification is in one or more codons encoding amino acid residues 33, 43, and/or 60 of the StxB1 protein. These modifications may give rise to amino acid substitutions of R33c, A43T, and G60D or equivalents. In yet another embodiment, such a modification is in one or more codons encoding amino acid residues 16 and/or 17 of StxB1 and in one or more codons encoding amino acid residues 33, 43, and/or 60 of the StxB1 protein. These modifications may give rise to amino acid substitutions of D16H and D17H or equivalents and amino acid substitutions of R33c, A43T, and G60D or equivalents.

Specifically contemplated are genomic DNA, cDNA, mRNA and antisense molecules, as well as nucleic acids based on alternative backbones, or including alternative bases, whether derived from natural sources or synthesized. Such nucleic acids, however, are defined further as being novel and unobvious over any prior art nucleic acid including that which encodes, hybridizes under appropriate stringency conditions, or is complementary to nucleic acid encoding a protein according to the present invention. Homology or identity at the nucleotide or amino acid sequence level is determined by BLAST (Basic Local Alignment Search Tool) analysis using the algorithm employed by the programs blastp, blastn, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference), which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a pre-selected threshold of significance. For a discussion of basic issues in similarity searching of sequence databases, please see Altschul et al. (1994) Nature Genetics 6, 119-129 which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992) Proc. Natl. Acad. Sci. USA 89, 10915-10919, fully incorporated by reference), recommended for query sequences over 85 in length (nucleotide bases).

For blastn, the scoring matrix is set by the ratios of M (i.e., the reward score for a pair of matching residues) to N (i.e., the penalty score for mismatching residues), wherein the default values for M and N are +5 and 4, respectively. Four blastn parameters were adjusted as follows: Q=10 (gap creation penalty); R=10 (gap extension penalty); wink=1 (generates word hits at every $wink^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Stringent conditions" are those that (1) employ low ionic strength and high temperature for washing, for example, 0.015 M NaCl/0.0015 M sodium citrate/0.1% SDS at 50° C. to 68° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer (pH 6.5) with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS or 68° C. in 0.1×SSC and 0.5% SDS. A skilled artisan can readily determine and vary the stringency conditions appropriately to obtain a clear and detectable hybridization signal. Preferred molecules are those that hybridize under the above conditions to the complement of SEQ ID NO: 1 and which encode a functional protein. Even more preferred hybridizing molecules are those that hybridize under the above conditions to the complement strand of the open reading frame of the nucleic acid encoding the chimeric Shiga toxoid that contains an enzymatically-inactivated StxA2 subunit and the native StxB1 subunit. As used herein, a nucleic acid molecule is said to be "isolated" when the nucleic acid molecule is substantially separated from contaminant nucleic acid molecules encoding other polypeptides.

The nucleic acid molecule encoding a chimeric Shiga toxoid containing an enzymatically-inactivated StxA2 subunit and the native StxB1 subunit, are part of an operon. One embodiment of the invention is an operon fusion composed of a nucleic acid encoding an enzymatically-inactivated StxA2 subunit followed by a nucleic acid molecule encoding the native $stxB_1$ intergenic region that contains the ribosomal binding site for translation of StxB1 and then a nucleic acid molecule encoding native StxB1.

The present invention further provides for fragments of the encoding nucleic acid molecule that contain a chimeric Shiga toxoid containing an enzymatically-inactivated StxA2 subunit and the native StxB1 subunit. As used herein, a fragment of an encoding nucleic acid molecule refers to a small portion of the entire protein coding sequence. The size of the fragment will be determined by the intended use. For instance, fragments which encode peptides corresponding to predicted antigenic regions may be prepared. If the fragment is to be used as a nucleic acid probe or PCR primer, then the fragment length is chosen so as to obtain a relatively small number of false positives during probing/priming.

Fragments of the encoding nucleic acid molecules of the present invention (i.e., synthetic oligonucleotides) that are used to synthesize gene sequences encoding proteins of the invention, can easily be synthesized by chemical techniques, for example, the phosphotriester method of Matteucci et al. (1981) J. Am. Chem. Soc. 103, 3185-3191 or using automated synthesis methods. In addition, larger DNA segments can readily be prepared by well-known methods, such as synthesis of a group of oligonucleotides that define various modular segments of the gene, followed by ligation of oligonucleotides to build the complete modified gene. In one embodiment, the nucleic acid molecule of the present invention contains a contiguous open reading frame of at least about 1,253 nucleotides, this sequence starting with the optimized Shine-Dalgarno sequence and ending after the $stxB_1$ stop codon.

The encoding nucleic acid molecules of the present invention may further be modified so as to contain a detectable label for diagnostic and probe purposes. The encoding nucleic acid molecules of the present invention may further be modified to contain a label for isolation such as e.g. by adding repeat codons encoding histidine molecules for use in e.g., nickel affinity purification. A variety of such labels are known in the art and can readily be employed with the encoding molecules herein described. Suitable labels include, but are not limited to, biotin, radiolabeled nucleotides, and the like. A skilled artisan can readily employ any such label to obtain labeled variants of the nucleic acid molecules of the invention. Modifications to the primary structure itself by deletion, addition, or alteration of the amino acids incorporated into the protein sequence during translation can be made without destroying the activity of the protein.

In one embodiment, a six histidine tag is added to the C-terminus of the native or slightly modified StxB1 protein to aid in purification of the StxA2/StxB1 toxoid by e.g. nickel affinity methods. In another embodiment, a six histidine tag is added to the C-terminus of the native or slightly modified StxB1 protein and six histidine tag is also added to the StxA2 protein. The histidine tag in the StxA2 protein may be located in the immediate vicinity of two histidines present at positions 244 and 245 of StxA2. The histidine tag may be added by making up to four amino acid changes in the StxA2 protein such as e.g., Q246H, G247H, A248H and R49H. Advantageously, the individual tagging of the StxA2 and StxB1 subunits allows for better purification of the subunits using ion exchange and size exclusion purifications procedures in conjunction with the nickel-affinity column purification.

Recombinant Nucleic Acids and Methods of Use

The present invention further provides recombinant nucleic acid molecules (e.g., DNA, RNA) that contain a coding sequence for a chimeric enzymatically-inactivated StxA2 subunit and the native StxB1 subunit. As used herein, a "recombinant nucleic acid molecule" is a nucleic acid molecule that has been subjected to molecular manipulation in situ. Methods for generating recombinant nucleic acid molecules are well known in the art, for example, see Sambrook et al. (2001) Molecular Cloning—A Laboratory Manual, Cold Spring Harbor Laboratory Press. In the preferred recombinant nucleic acid molecules, a coding nucleotide sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably, also expression, of the structural gene included in the recombinant nucleic acid molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical examples of such vector plasmids are pBluescript II KS(-) (Stratagene), pTrcHis2C (Invitrogen), pUC8, pUC9, pBR322 and pBR329 (BioRad), pPL and pKK223 (Pharmacia).

Expression vectors compatible with eukaryotic cells, preferably those compatible with vertebrate cells, can also be used to form recombinant nucleic acid molecules that contain a coding sequence. Eukaryotic cell expression vectors, including viral vectors, are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies Inc.), pTDT1 (ATCC), the vector pCDM8 described herein, and the like eukaryotic expression vectors.

Eukaryotic cell expression vectors used to construct the recombinant nucleic acid molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene (Southern et al. (1982) J. Mol. Anal. Genet. 1, 327-341). Alternatively, the selectable marker can be present on a separate plasmid, and the two vectors are introduced by co-transfection of the host cell, and selected by culturing in the appropriate drug for the selectable marker. The present invention further provides host cells transformed with a nucleic acid molecule that encodes a protein of the present invention. The host cell can be either prokaryotic or eukaryotic.

Eukaryotic cells useful for expression of a chimeric protein of the invention are not limited, so long as the cell line is compatible with cell culture methods and compatible with the propagation of the expression vector and expression of the gene product. Suitable eukaryotic host cells include, but are not limited to, yeast, insect, and mammalian cells, preferably vertebrate cells such as those from a mouse, rat, monkey, or human cell line. Exemplary eukaryotic host cells include Chinese hamster ovary (CHO) cells available from the ATCC as CCL61, NIH Swiss mouse embryo cells (NIH-3T3) available from the ATCC as CRL 1658, baby hamster kidney cells (BHK), and the like eukaryotic tissue culture cell lines.

Any prokaryotic host can be used to express a recombinant nucleic acid molecule encoding a chimeric protein of the invention. In one embodiment, the prokaryotic host is *E. coli* such as strain DH5α or BL21. In alternate embodiments, the prokaryotic host is a live attenuated oral bacterial vaccine strain, such as *Shigella flexneri* (Barry et al. (2003) Vaccine 21, 33340) or *V. cholerae* (Leyten et al. (2005) Vaccine 23, 5120-5126).

Transformation of appropriate cell hosts with an rDNA molecule of the present invention is accomplished by well known methods that typically depend on the type of vector used and host system employed. With regard to transformation of prokaryotic host cells, electroporation and salt treatment methods are typically employed, see, for example, Cohen et al. (1972) Proc. Natl. Acad. Sci. USA 69, 2110; and Sambrook et al. (2001) Molecular Cloning—A Laboratory Manual, Cold Spring Harbor Laboratory Press. With regard to transformation of vertebrate cells with vectors containing rDNA, electroporation, cationic lipid or salt treatment methods are typically employed, see, for example, Graham et al. (1973) Virol. 52, 456; Wigler et al. (1979) Proc. Natl. Acad. Sci. USA 76, 1373-1376.

Successfully transformed cells, i.e., cells that contain a recombinant nucleic acid molecule of the present invention, can be identified by well known techniques including the selection for a selectable marker. For example, cells resulting from the introduction of a recombinant nucleic acid of the present invention can be cloned to produce single colonies. Cells from those colonies can be harvested, lysed and their nucleic acid content examined for the presence of the recombinant nucleic acid using a method such as that described by Southern (1975) J. Mol. Biol. 98, 503-504 or Berent et al. (1985) Biotech. 3, 208-209 or the proteins produced from the cell assayed via an immunological method.

Production of Recombinant Proteins

One skilled in the art would know how to make recombinant nucleic acid molecules which encode chimeric Shiga toxoids of the invention. Furthermore, one skilled in the art would know how to use these recombinant nucleic acid molecules to obtain the proteins encoded thereby, as described herein for the recombinant nucleic acid molecule, which encodes a hybrid Shiga toxoid.

In accordance with the invention, numerous vector systems for expression of the hybrid Shiga toxoid may be employed. For example, one class of vectors utilizes DNA elements, which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells, which have stably integrated the DNA into their chromosomes, may be selected by introducing one or more markers, which allow for the selection of transfected host cells. The marker may provide, for example, prototropy to an auxotrophic host, biocide resistance, (e.g., antibiotics) or resistance to heavy metals such as copper or the like. The selectable marker gene can be either directly linked to the DNA sequences to be expressed, or introduced into the same cell by co-transformation. Additional elements may also be needed for optimal synthesis of mRNA. These elements may include splice signals, as well as transcriptional promoters, enhancers, and termination signals. The cDNA expression vectors incorporating such elements include those described by Okayama (1983) Mol. Cell. Biol. 3, 280-289.

The hybrid Shiga toxoid may be produced by (a) transfecting a cell with an expression vector encoding the hybrid Shiga toxoid; (b) culturing the resulting transfected cell under conditions such that the hybrid Shiga toxoid is produced; and (c) recovering the hybrid Shiga toxoid from the cell culture media or the cells themselves.

Once the expression vector or DNA sequence containing the constructs has been prepared for expression, the expression vectors may be transfected or introduced into an appropriate eukaryotic or prokaryotic cell host. Various techniques may be employed to achieve this, such as, for example, protoplast fusion, calcium phosphate precipitation, electroporation or other conventional techniques. In the case of protoplast fusion, the cells are grown in media and screened for the appropriate activity.

Methods and conditions for culturing the resulting transfected cells and for recovering the hybrid Shiga toxoid so produced are well known to those skilled in the art, and may be varied or optimized depending upon the specific expression vector and host cell employed.

The host cell for expressing the hybrid Shiga toxoid may be prokaryotic or eukaryotic. Exemplary prokaryotic hosts include *E. coli*, such as *E. coli* DH5α or BL21. Exemplary eukaryotic hosts include baculovirus vector/insect cell expression systems, yeast shuttle vector/yeast cell expression systems. Methods and conditions for purifying the hybrid Shiga toxoid from the culture media are provided in the invention, but it should be recognized that these procedures can be varied or optimized as is well known to those skilled in the art.

The hybrid Shiga toxoid proteins of the present invention may also be prepared by any known synthetic techniques. Conveniently, the proteins may be prepared using the solid-phase synthetic technique initially described by Merrifield (1965), which is incorporated herein by reference. Other peptide synthesis techniques may be found, for example, in Bodanszky et al. (1976), Peptide Synthesis, Wiley.

Immunogenic Compositions and Uses Thereof

The chimeric hybrid Shiga toxoid of the invention may be used in a vaccine, immunogenic or pharmaceutical composition to generate an immune response against a Stx. The chimeric Shiga toxoid can also be used in combination with other less immunogenic compositions to assist in eliciting an immune response against the immunogenic compositions. Generally, when used in combination with another immunogenic composition, the immunogenic composition by itself is not sufficient to elicit an immune response and provide a protective effect against a pathogen. In one embodiment, the Shiga toxoids of the invention are used in combination with diphtheria toxin as a means for providing a protective effect against infection by *Corynebacterium diphtheriae*.

In one embodiment, the hybrid Shiga toxoid is used with a suitable adjuvant, as generally understood in the art. Currently, adjuvants approved for human use in the United States include e.g., aluminum salts (alum). These adjuvants have been useful for some vaccines including hepatitis B, diphtheria, polio, rabies, and influenza. Other useful adjuvants include Complete Freund's Adjuvant (CFA), Muramyl dipeptide (MDP), synthetic analogues of MDP, N-acetylmuramyl-L-alanyl-D-isoglutamyl-L-alanine-2-[1,2-dipalmitoyl-s-glycero-3-(hydroxyph osphoryloxy)]ethylamide (MTP-PE), Incomplete Freund's Adjuvant (IFA), and compositions containing a degradable oil and an emulsifying agent, wherein the oil and emulsifying agent are present in the form of an oil-in-water emulsion having oil droplets substantially all of which are less than one micron in diameter.

The formulation of a vaccine, immunogenic or pharmaceutical compositions of the invention will employ an effective amount of the chimeric Shiga toxoid. That is, there will be included an amount of antigen which, in combination with the adjuvant, will cause the subject to produce a specific and sufficient immunological response so as to impart protection to the subject from subsequent exposure to Stx. When used as an immunogenic composition, the formulation will contain an amount of antigen, which, in combination with the adjuvant, will cause the subject to produce specific antibodies, which may be used for diagnostic or therapeutic purposes.

The vaccine, immunogenic or pharmaceutical compositions of the invention may be useful for the prevention or therapy of hemolytic uremic syndrome (HUS) and/or for the treatment of diarrhea. In one embodiment, the vaccine and/or immunogenic composition are used for the prevention of HUS in the elderly and children. In another embodiment, the vaccine and/or immunogenic composition are used for the prevention of HUS or other consequences of STEC infection or Stx intoxication caused by acts of terrorism, especially for administration to military personnel. Often, more than one administration may be required to bring about the desired prophylactic or therapeutic effect; the exact protocol (dosage and frequency) can be established by standard clinical procedures.

The hybrid Shiga toxoid or pharmaceutical compositions comprising the hybrid Shiga toxoid of the present invention can be administered via parenteral, subcutaneous, intravenous, intramuscular, intraperitoneal, transdermal or buccal routes. Alternatively, or concurrently, administration may be by the oral route. In one embodiment particularly suitable for children, a pharmaceutical composition comprising the Shiga toxoid is administered by the oral route. The dosage administered will be dependent upon the age, health, and weight of the recipient, kind of concurrent treatment, if any, frequency of treatment, and the nature of the effect desired.

The pharmaceutical compositions of the present invention may contain suitable pharmaceutically acceptable carriers comprising excipients and auxiliaries that facilitate processing of the active compounds into preparations, which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances, which increase the viscosity of the suspension, for example, sodium carboxymethyl cellulose, sorbitol and dextran. Optionally, the suspension may also contain stabilizers.

The precise amounts and formulations for use in either prevention or therapy can vary depending on the circumstances of the inherent purity and activity of the antigen, any additional ingredients, or carriers, the method of administration and the like.

The pharmaceutical formulation for systemic administration according to the invention may be formulated for enteral, parenteral, or topical administration. Indeed, all three types of formulations may be used simultaneously to achieve systemic administration of the active ingredient.

Topical administration may be used. Any common topical formulation such as a solution, suspension, gel, ointment or salve and the like may be employed. Preparation of such topical formulations are described in the art of pharmaceutical formulations as exemplified, for example, by Gennaro et al. (2000) Remington's Pharmaceutical Sciences, Mack Publishing. For topical application, the compositions could also be administered as a powder or spray, particularly in aerosol form.

Suitable formulations for oral administration include hard or soft gelatin capsules, pills, tablets, including coated tablets, elixirs, suspensions, syrups or inhalations and controlled release forms thereof.

By way of non-limiting illustration, the vaccine dosages administered will typically be, with respect to the antigen, a minimum of about 0.1 mg/dose, more typically a minimum of about 1 mg/dose, and often a minimum of about 10 mg/dose. The maximum dosages are typically not as critical. Usually, however, the dosage will be no more than 500 mg/dose, often no more than 250 mg/dose. These dosages can be suspended in any appropriate pharmaceutical vehicle or carrier in sufficient volume to carry the dosage. Generally, the final volume, including carriers, adjuvants, and the like, typically will be at least 0.1 ml, more typically at least about 0.2 ml. The upper limit is governed by the practicality of the amount to be administered, generally no more than about 0.5 ml to about 1.0 ml.

In an alternative format, vaccine, immunogenic or pharmaceutical compositions may be prepared as vaccine vectors, which express the chimeric hybrid Shiga toxoid or fragment thereof in the host animal. Any available vaccine vector may be used, including live Venezuelan Equine Encephalitis virus (see U.S. Pat. No. 5,643,576), poliovirus (see U.S. Pat. No. 5,639,649), pox virus (see U.S. Pat. No. 5,770,211) and vaccine virus (see U.S. Pat. Nos. 4,603,112 and 5,762,938). Alternatively, naked nucleic acid encoding the protein or fragment thereof may be administered directly to effect expression of the antigen (see U.S. Pat. No. 5,739,118).

In one embodiment of the invention, a nucleotide encoding the hybrid Shiga toxoid is transformed into a live attenuated oral bacterial vaccine strain such as e.g. Shigella flexneri (Barry et al. (2003) Vaccine 21, 33340) or V. cholerae (Leyten et al. (2005) Vaccine 23, 5120-5126). Thus, such oral bacterial vaccine strains would have expanded protective coverage to include the Stx.

In another embodiment of the invention, a nucleotide encoding the hybrid Shiga toxoid is transformed into a plant to create an edible plant-based vaccine. Alternatively, a nucleotide encoding the hybrid Shiga toxoid could be administered as a DNA-based vaccine. Nucleic acids encoding the chimeric toxoids are administered as DNA vaccines, as either a single genes or combinations of genes. Naked DNA vaccines are generally known in the art (see Brower (1998), Nature Biotechnology, 16:1304-1305). Methods for the use of genes as DNA vaccines are well known to one of ordinary skill in the art, and include placing a chimeric toxoid gene or portion thereof under the control of a promoter for expression in a subject in need of treatment. The gene used for DNA vaccines can encode full-length chimeric toxoid proteins, but may also encode portions of the toxoid proteins including peptides derived from the any Shiga toxin gene. The DNA vaccine may contain A and B subunit genes for expression as individual operons under the direction of individual and/or distinct promoters and include rearranging the order of the two coding regions. Modifications made to the nucleotide sequences such as the incorporation of 5' and 3' untranslated regions of viral or eukaryotic origin, polyadenylation signals, codon optimization for optimal expression in a eukaryotic system are also encompassed in the invention. In one embodiment, a subject is immunized with a DNA vaccine comprising a plurality of nucleotide sequences encoding a chimeric toxoid protein.

Similarly, it is possible to immunize a subject with a plurality of toxoid genes or portions thereof as defined herein.

In another embodiment, the DNA vaccines include a gene encoding an adjuvant molecule with the DNA vaccine. Such adjuvant molecules include cytokines that increase the immunogenic response to the toxoid protein encoded by the DNA vaccine. Additional or alternative adjuvants are known to those of ordinary skill in the art and find use in the invention. Alternatively, the chimeric toxoid gene itself may serve as an adjuvant in a DNA vaccine containing a nucleic acid encoding another different immunogen.

The hybrid Shiga toxoid may be used in combination, e.g., simultaneously, with vaccines for other diseases. Thus, the hybrid Shiga toxoid may be part of a composition for the treatment and prevention of dysentery and diarrhea, including traveler's diarrhea Such a composition would be particularly useful for children in third world countries who are exposed to Stx and/or bacteria expressing Stx. The effects of Stx in children tend to be severe leading in some instances to permanent renal damage. Prevention of infection and subsequent exposure to Stx in children is therefore a preferred use for the chimeric Shiga toxoid proteins of the invention.

Antibodies and Methods of Use

This invention further provides for a polyclonal antibody directed to at least one epitope of the StxA2 subunit and at least one epitope of StxB1 subunit and capable of preventing, treating, or diagnosing hemolytic uremic syndrome.

The antibodies of the invention may be labeled with a detectable marker. Detectable markers useful in the practice of this invention are well known to those of ordinary skill in the art and may be, but are not limited to radioisotopes, dyes, or enzymes such as peroxidase or alkaline phosphatase, and nanoparticles. Antibodies labeled with detectable markers are particularly useful for diagnosis. The kit may further contain monoclonal or polyclonal anti-StxA2 and anti-StxB1 antibodies that are labeled with a detectable marker and other substituents well known to the art. Such a kit is particularly useful for the detection of Stx or Stx-producing bacteria such as *S. dysenteriae* and *E. coli* in vitro and in vivo and for the diagnosis of HUS.

This invention also concerns an anti-idiotypic antibody directed against the human polyclonal antibodies. This anti-idiotypic antibody may also be labeled with a detectable marker. Suitable detectable markers are well known to those of ordinary skill in the art and may be, but are not limited to radioisotopes, dyes, or enzymes such as peroxidase or alkaline phosphatase.

The anti-idiotypic antibody is produced when an animal is injected with a polyclonal antibody, which binds to at one epitope of the StxA2 subunit and at least one epitope of StxB1 subunit. The animal will then produce antibodies directed against the idiotypic determinants of the injected antibody (Wasserman et al. (1982), Proc. Natl. Acad. Sci. 79, 4810-4814).

Alternatively, the anti-idiotypic antibody is produced by: (1) contacting lymphoid cells of an animal with an effective-antibody raising amount of the antigen (i.e., the polyclonal antibody which binds to at one epitope of the StxA2 subunit and at least one epitope of StxB1 subunit); (2) collecting the resulting lymphoid cells; fusing the collected lymphoid cells with myeloma cells to produce a series of hybridoma cells, each of which produces a monoclonal antibody; (3) screening the series of hybridoma cells to identify those which secrete a monoclonal antibody capable of binding the resulting hybridoma cell so identified; and (4) separately recovering the anti-idiotypic antibody produced by this cell (Cleveland et al. (1983) Nature 305, 56-57). Animals, which may be used for the production of anti-idiotypic antibodies in either of the two above-identified methods, include, but are not limited to humans, primates, mice, rats, or rabbits.

Diagnostic Assays

The hybrid Shiga toxoid of the present invention may be used as diagnostic reagents in immunoassays to detect anti-Stx antibodies, particularly anti-StxA2 antibodies and anti-StxB1 antibodies. Immunoassay protocols may be based, for example, upon composition, direct reaction, or sandwich-type assays. Protocols may also, for example, be heterogeneous and use solid supports, or may be homogeneous and involve immune reactions in solution. Most assays involved the use of labeled antibody or polypeptide. The labels may be, for example, fluorescent, chemiluminescent, radioactive, nanoparticles, or dye molecules. Assays which amplify the signals from the probe are also known, examples of such assays are those which utilize biotin and avidin, and enzyme-labeled and mediated immunoassays, such as ELISA assays.

Typically, an immunoassay for anti-Stx antibodies will involve selecting and preparing the test sample, such as a biological sample, and then incubating it with a modified hybrid Shiga toxoid of the present invention under conditions that allow antigen-antibody complexes to form. Such conditions are well known in the art. In a heterogeneous format, the protein or peptide is bound to a solid support to facilitate separation of the sample from the polypeptide after incubation. Examples of solid supports that can be used are nitrocellulose, in membrane or microtiter well form, polyvinylchloride, in sheets or microtiter wells, polystyrene latex, in beads or microtiter plates, polyvinylidine fluoride, diazotized paper, nylon membranes, activated beads, and Protein A beads. Most preferably, Dynatech, Immulon® microtiter plates, or 0.25 inch polystyrene beads are used in the heterogeneous format. The solid support is typically washed after separating it from the test sample.

In homogeneous format, on the other hand, the test sample is incubated with the hybrid Shiga toxoid in solution, under conditions that will precipitate any antigen-antibody complexes that are formed, as is known in the art. The precipitated complexes are then separated from the test sample, for example, by centrifugation. The complexes formed comprising anti-Stx antibodies are then detected by any number of techniques. Depending on the format, the complexes can be detected with labeled anti-xenogenic immunoglobulin or, if a competitive format is used, by measuring the amount of bound, labeled competing antibody. These and other formats are well known in the art.

Diagnostic probes useful in such assays of the invention include antibodies to Stx. The antibodies may be either monoclonal or polyclonal produced using standard techniques well known in the art (see Harlow & Lane (1988), Antibodies: A Laboratory Manual, Cold Spring Harbor Laboratory Press). They can be used to detect Stx by specifically binding to the protein and subsequent detection of the antibody-protein complex by ELISA, Western blot or the like. The hybrid Shiga toxoid used to elicit these antibodies can be any of the variants discussed above. Antibodies are also produced from peptide sequences of the hybrid Shiga toxoid using standard techniques in the art (Harlow & Lane, supra). Fragments of the monoclonals or the polyclonal antisera, which contain the immunologically significant portion, can also be prepared.

The following working examples specifically point out preferred embodiments of the present invention, and are not to be construed as limiting in any way the remainder of the disclosure. Other generic configurations will be apparent to one skilled in the art.

EXAMPLES

Example 1

Construction of Chimeric stxA$_2$/stxB$_1$ and Toxoid Mutations

A genetically toxoided version of Stx that could be used as a vaccine to protect against both Stx1 and Stx2 was constructed. Because the StxB1 protein is highly immunogenic and more protective than the StxB2 subunit protein (Marcato et al. (2001) J. Infect. Dis. 183, 435-43), StxB1 was used for the B subunit portion of the vaccine. StxA2 was chosen for the A subunit of the vaccine construct.

The stxA$_2$ and stxB$_1$ genes were spliced together to generate an operon fusion composed of stxA$_2$ followed by the native stxB$_1$ intergenic region that contains the ribosomal binding site for translation of StxB1, then the stxB$_1$ gene. The holotoxoid expression cassette was designed in the native operon configuration to optimize translation and assembly of the AB5 holotoxoid.

Next, the StxA2 portion of the chimeric toxoid was modified by introducing three modifications (Y77S, E167Q, and R170L) to prevent a potential for reversion to toxicity and to maximize immunogenicity. The selection of these mutations was based on prior studies that showed that these mutations either reduced the cytotoxicity of the toxin or increased the immunogenicity of a toxoid. The substitution of tyrosine at position 77 to serine was generated because this change substantially reduces the activity of Stx1, and we predicted that the same would be true for Stx2 (Deresiewicz et al. (1992) Biochemistry 31, 3272-80; Deresiewicz et al. (1993) Mol. Gen. Gent. 241, 467-73). The decision to change the glutamic acid at position 167 of Stx2 to glutamine was done because this amino acid is in the active site of both Stx1 and Stx2 and such an alteration leads to a dramatic reduction in the Vero cell activity of the toxin (Gordon et al. (1992) Infect. Immun. 65, 2509-16; Hovde et al. (1988) Proc. Natl. Acad. Sci. USA 85 2568-72; Jackson et al. (1990) J Bacteriol 182, 3346-50; Yamaski et al. (1991) Mircob. Pathog. 11, 1-9). The choice to replace arginine at position 170 with leucine reflects the Ishikawa et al. observation that the StxA1 protein is more immunogenic after such a substitution (Ishikawa et al. (2003) Infect Immun 71, 3235-9). A detailed description of the methodology follows.

Bacterial plasmids used are listed in Table 1. Bacteria were grown in Luria-Bertani (LB) broth or on LB agar (Becton Dickinson) supplemented with 100 μg/ml of ampicillin as needed for selection of recombinant plasmids.

TABLE 1

Cloning and Expression Plasmids

| | |
|---|---|
| pBluescript SK II | E. coli cloning vector (Amp$^r$) |
| pTrcHisZ C | E. coli expression vector (Amp$^r$) |
| pCKS112 | stx$_1$ clone |
| pJES120 | stx$_2$ clone |
| pMJS1 | pBluescript II KS (-) clone of stx$_1$ from pCKS112 |
| pMJS2 | pBluescript II KS (-) clone of stx$_2$ from pJES120 |
| pMJS21 | pBluescript II KS (-) clone of stxA$_2$/stxB$_1$ |
| pMJS22 | pMJS21 with StxA2 Y77S mutation |
| pMJS23 | pMJS22 with StxA2 E167Q and R170L mutations |
| pMJS24 | stxA$_2$/stxB$_1$ toxoid clone from pMJS23 cloned into pTrcHis2 C |
| pMJS25 | TA-cloning vector pCR2.1 clone of pMJS23 with StxA2 E167Q change from CAA (Q) to CAG (Q) |
| pMJS26 | pTrcHis2 C clone of the stxA$_2$/stxB$_1$ toxoid clone made on pMJS25 with six histidines added to the C-terminus of StxB1. |
| pMJS27 | pTrcHis2 C clone of the stxA$_2$/stxB$_1$ toxoid clone made on pMJS26 with StxB1 D16H and D17H mutations |

The chimeric stxA$_2$/stxB$_1$ operon was created by a series of polymerase chain reactions (PCR) followed by a splicing by overlap extension (SOE) step (Higuchi et al. (1989), PCR Technology, Stockton Press). Specifically, PCR amplification of sequences from pMJS2 with primers MJS5 and MJS32 (see Table 2) was used to synthesize stxA$_2$; similarly, PCR amplification of sequences from pMJS1 with primers MJS20 and MJS2 was used to generate stxB$_1$. After the stxA$_2$ and stxB$_1$ PCR products were spliced together, the chimeric stxA$_2$/stxB$_1$ operon was cloned into pBluescript II KS$^-$ (Stratagene) under direction of the stx$_2$ promoter. The resultant plasmid was named pMJS21 and transformed into E. coli DH5α.

TABLE 2

Synthetic oligonucleotide primers (5' to 3')

| Primer | Primer Sequence (5' to 3') | Purpose/Region of homology |
|---|---|---|
| MJS1 | gatcggatcccctgtaacgaagtttgcgtaacagc (SEQ ID NO: 4) | stx$_1$ upstream primer |
| MJS2 | gatcgaattctcgcttacgatcatcaaagagatcatacc (SEQ ID NO: 5) | stx$_1$ downstream primer |
| MJS5 | gatcggatccagcaagggccaccatatcacataccgcc (SEQ ID NO: 6) | stx$_2$ upstream primer |
| MJS6 | cagggaattcaccatgcgaaattttttaacaaatgc (SEQ ID NO: 7) | stx$_2$ downstream primer |
| MJS20 | gggggtaaaatgaaaaaaacattattaatagc (SEQ ID NO: 8) | Used with MJS32 to generate pMJS21 |
| MJS32 | gctattaataatgttttttcattttaccccttatttacccgttgtatataaaaactg (SEQ ID NO: 9) | Used with MJS20 to generate pMJS21 |

TABLE 2-continued

Synthetic oligonucleotide primers (5' to 3')

| Primer | Primer Sequence (5' to 3') | Purpose/Region of homology |
|---|---|---|
| MJS88 | tcagtggccgggttcgttaatacgg (SEQ ID NO: 10) | Used with MJS89 to generate pMJS22 |
| MJS89 | ccgtattaacgaacccggccactgataaattattttgctcaataatcagacgaagatggtc (SEQ ID NO: 11) | Used with MJS88 to generate pMJS22 |
| MJS90 | caagccttattattcaggcagatacagagagaatttcgtcaggc (SEQ ID NO: 12) | Used with MJS91 to generate pMJS23 |
| MJS91 | ctctgtatctgcctgaataataaggcttgtgctgtgacagtgacaaaacgcagaactgctctgg (SEQ ID NO: 13) | Used with MJS90 to generate pMJS23 |
| 2A5SD | gatc<u>ggatcc</u>taaggaggacagctatgaagtgtatattatttaaatgggtactg (SEQ ID NO: 14) | Used to generate pMJS24, pMJS26, and pMJS27 |
| MJS97 | gat<u>catcgat</u>agccaaaaggaacacctgtatatg (SEQ ID NO: 15) | stxA₂ upstream primer, used to generate pMJS25 |
| MJS98F | gatc<u>gctagc</u>tcaacgaaaaataacttcgctgaatcc (SEQ ID NO: 16) | stxB₁ downstream primer used to generate pMJS25 |
| MJS92 | caggccttattattcaggcag (SEQ ID NO: 17) | Used with MJS93 to generate pMJS25 |
| MJS93 | ctgcctgaataataaggcctgtgctgtgacagtgacaaaacgcagaactgctctggatgc (SEQ ID NO: 18) | Used with MJS92 to generate pMJS25 |
| 1BC1 | ggtggtggtgacgaaaaataacttcgctgaatcc (SEQ ID NO: 19) | stxB₁ His-tagged downstream primer #1, used to generate pMJS26 and pMJS27 |
| 1BC2 | cagtggtggtggtggtggtgacgaaaaataac (SEQ ID NO: 20) | stxB₁ His-tagged downstream primer #2, used to generate pMJS26 and pMJS27 |
| 1BC3 | gatc<u>gaattc</u>tcagtggtggtggtggtg (SEQ ID NO: 21) | stxB₁ His-tagged downstream primer #3, used to generate pMJS26 and pMJS27 |
| 1B2HF | catcacgatacctttacagttaaagtggg (SEQ ID NO: 22) | Used with 1B2HR to generate pMJS27 |
| 1B2HR | tttaactgtaaaggtatcgtgatgattatattttgtatactccacc (SEQ ID NO: 23) | Used with 1B2HF to generate pMJS27 |

Restriction enzyme sites are underlined, Mutagenic codon sites are in bold.

Next, a set of nucleotide changes were engineered into the stxA₂ gene of stxA₂/stxB₁ to generate an operon from which a hybrid toxoid molecule could be expressed. Specifically, the tyrosine at position 77 of the StxA2 mature protein was changed to a serine residue by amplification of the DNA with mutagenic primers MJS88 and MJS89 and flanking primers MJS2 and MJS5 to yield pMJS22. Then the glutamic acid at the active site of StxA2 (residue 167) was altered to a glutamine and the arginine at position 170 was changed to a lysine simultaneously by PCR with mutagenic primers MJS90 and MJS91 and flanking primers MJS2 and MJS5 to yield pMJS23. The chimeric toxoid operon was then amplified from pMJS23 by PCR with the 2A5 SD and MJS2 primers to introduce an optimized Shine-Dalgarno sequence (TA AGGAGGACAGCTATG) (SEQ ID NO: 24) upstream of the start codon for StxA2 and to remove the native stx₂ promoter. The resulting chimeric clone was ligated into the expression vector pTrcHis2 C (Invitrogen) and transformed into E. coli strain BL21 (DE3). DNA sequence analysis was done by the Biomedical Instrumentation Center at the Uniformed Services University to verify that the correct mutations were made.

Example 2

Purification of the StxA2/StxB1 Toxoid

The purification of the StxA2/StxB1 toxoid was done by Gb3 affinity purification as described previously (Ishikawa et al. (2003) Infect. Immun. 71, 3235-9; Wen et al. supra). Gb3 affinity purification is a process that captures the B subunit binding domain. An overnight culture of E. coli BL21 (DE3) that contained the pTrcHis2 C-stxA₂/stxB₁ clone was diluted 1:50 into two flasks each containing 500 ml LB broth. After 2 hours of growth, the cultures were induced with 1 mM isopropyl 3-D-thiogalactopyranoside (IPTG) and incubated for an additional 4 hours.

The bacteria were pelleted by centrifugation and concentrated 50-fold by re-suspension in 10 ml of 1× phosphate-buffered saline, pH 7.4 (PBS). The concentrated bacterial suspensions were then disrupted by sonication and the resulting lysates clarified by centrifugation. The StxA2/StxB 1 toxoid was purified from these lysates by Gb3 affinity purification on Globotriose Fractogel columns (IsoSep AB) as described previously (Ishikawa et al., supra; Wen et al., supra). After purification of the toxoid, a BCA assay (Pierce) was done to quantify the protein concentration of the preparation.

Example 3

Cytotoxicity Assay

The cytotoxic activity for Vero cells of various samples was assessed as previously described. Briefly, *E. coli* DH5 α, transformed with toxin clones in pBluescript II KS (–) were normalized to the same optical density $(O.D.)_{600}$, and the bacteria were disrupted by sonication and clarified by centrifugation. Clarified sonic lysates or purified toxoid were assessed for Vero cell cytotoxic activity (Schmitt et al. (1991) Infect. Immun. 59, 1065-73; Gentry et al. (1980) 26, 2127-31) after diluting the samples in Eagle's minimum essential medium (Cambrex BioScience) supplemented with 9% fetal bovine serum (BioSource International), 1.8 mM glutamine (Cambrex), 9 U/ml of penicillin 9 pg/ml of streptomycin (Invitrogen Corporation), and 90 μg/ml of gentamicin (Quality Biological) (complete EMEM). The 50% cytotoxic dose ($CD_{50}$) of samples was defined as the reciprocal of the dilution that killed 50% of the Vero cells, as compared to the untreated control cells.

The cytotoxic activities of the different versions of the mutated StxA2/StxB1 toxoids for Vero cells were compared to the parent StxA2/StxB1 toxin (see Table 3). While one ml of a clarified sonic lysate of the parent hybrid toxin contained $7.2\times10^4$ $CD_{50}$s, similarly prepared lysates of the altered chimeric molecule with either a single mutation (Y77S) or the triple mutations (Y77S, E167Q and R170L) had no demonstrable cytotoxic activity, a finding that confirmed that these constructs produced toxoids. Additionally, 2.1 μg of the purified StxA2/StxB1 toxoid was not cytotoxic to Vero cells; this was approximately 97 times the concentration of the parent StxA2/Stx1B toxin assayed. The quantity of the parent StxA2/Stx1 B toxin was determined by Western blot analysis using polyclonal antibody against Stx2 and quantifying StA2 subunit by comparison with an Stx2 standard. To determine if there was any residual activity at very low levels of the Stx2A/Stx1B toxoid, a 100-fold preparation of crude bacterial lysate was tested for cytotoxicity on Vero cells and for toxicity in mice. Five CD-1 male mice were injected intraperitoneally with 86 μg of the toxoid (this corresponds to 20 times the amount used to immunize and boost the mice) and all of the mice survived. Additionally, 61.3 μg of the toxoid from the 100-fold preparation crude bacterial lysate was tested for cytotoxicity and was found to be non-cytotoxic to Vero cells.

TABLE 3

Results of the Cytotoxic assay

| Toxin or toxoid | Cytotoxicity (Vero cell $CD_{50}$/ml of culture) |
|---|---|
| pBluescript II (KS-) | $<1\times10^2$ |
| Stx1 | $8.1\times10^6$ |
| Stx2 | $5.5\times10^4$ |
| StxA2/StxB1 | $7.2\times10^4$ |
| StxA2/StxB1 (Y77S) | $<1\times10^2$ |
| StxA2/StxB1 (Y77S, E167Q, R170L) | $<1\times10^2$ |
| StxA2/StxB1 toxoid (purified, 2.1 μg) | $<1\times10^2$ |

Toxin lysates were from *E. coli* DH5α transformed with pMJS1 (Stx1), pMJS2 (Stx2), pMJS21 (StxA2/StxB1), pMJS22 (StxA2/StxB1 with StxA2 Y77S), pMJS23 (StxA2/StxB1 with StxA2 Y77S, E167Q and R170L). The purified StxA2/Stx1 toxoid was purified from *E. coli* Bl21. The values represent the reciprocal of the dilution that killed 50% of the Vero cells. The limit of detection for this experiment was $1\times10^2$.

Example 4

Western Blot Analysis

Purified Stx1, Stx2 or the StxA2/StxB1 toxoid (300 ng each) were subjected to sodium dodecyl sulfate-polyacrylamide gel electrophoresis (SDS-PAGE; 15% polyacrylamide) and then the proteins were transferred to 0.45 μM Optitran nitrocellulose membranes (Schleicher & Schuell) with a Trans-Blot SD Semi-Dry transfer apparatus (Bio-Rad) (see FIG. 1). The membranes were blocked overnight at 4° C. in a solution of 5% non-fat dry milk in 1× Tris-buffered saline (pH 7.5) with 0.1% Tween 20 added (TBST). The primary antibodies, hybridoma tissue culture supernatants diluted 1:5 each in blocking solution of anti-StxA2 and anti-StxB1 monoclonal antibodies (MAbs) 11E10 and 13C4, respectively (Gentry et al. (1980) J. Clin. Microbiol. 12, 361-6; Perera et al. (1980) J. Clin. Microbiol. 26, 2127-31), were incubated with the immunoblots for two hours. The membranes were then washed in TBST and incubated for one hour with goat anti-mouse immunoglobin G (IgG) conjugated to horseradish peroxidase (HRP) (Bio-Rad) at a dilution of 1:3,000 in blocking solution. The membranes were washed again as described above, and the secondary antibody was detected by chemiluminescence with the ECL-Plus Western Blotting Detection kit (Amersham).

The immunoblot of the purified toxoid revealed both StxB1 and StxA2 were present (see FIG. 1), a finding that confirmed our supposition that a holotoxoid was expressed by the vaccine construct. In addition, the immunoreactive bands of the toxoid corresponded in size to the native toxin subunit controls (see FIG. 1). The StxA2 and StxB1 subunits were also visible on the silver stained-gel with little evidence of additional contaminating proteins (data not shown).

Example 5

Mouse Immunization and Challenge

Pre-immune sera were collected from male CD-1 mice that weighed 14 to 16 grams (Charles River). The mice were then immunized intraperitoneally (i.p.) with either PBS or 4.3 μg of purified StxA2/Stx11 toxoid in PBS mixed 1:1 with TiterMax Gold, a water-in-oil adjuvant (TiterMax USA) (total volume 100 μl). The mice were boosted at three-week intervals, for a total of three boosts. Serum was collected ten days after the initial immunization and after each boost to determine serum immunoglobin G (IgG) levels against Stx1 or Stx2. The mice were challenged i.p. 14 days after the third boost with 10 times the 50% lethal dose ($LD_{50}$) of either Stx1 (1,250 ng) or Stx2 (10 ng) or both Stx1 and Stx2 (1,250 and 10 ng/mouse, respectively).

All of the PBS-immunized mice died by day 4, regardless of the Stx type administered (see Table 4). All of the chimeric toxoid-immunized mice subsequently challenged with either Stx1 or Stx2 survived the entire 14 day observation period. Nine of the ten chimeric toxoid-immunized mice that were subsequently challenged with both Stx1 and Stx2 survived. The chimeric toxoid-immunized mouse that succumbed after challenge with lethal doses of both Stx1 and Stx2 was the mouse that also failed to produce anti-Stx1 and anti-Stx2 neutralizing antibodies; this mouse died at approximately the same time as did the mock-immunized animals. The $LD_{50}$ was previously determined to be 125 and 1 ng/mouse for Stx1 and Stx2. The average weight of the mice when they were challenged was 40.4 g.

TABLE 4

Protection of immunized mice against a lethal challenge

| Group | immunogen | challenge with 10 $LD_{50}$ | # survivors per total |
| --- | --- | --- | --- |
| A | PBS | Stx1 | 0/10 |
| B | StxA2/StxB1 toxoid | Stx1 | 10/10 |
| C | PBS | Stx2 | 0/10 |
| D | StxA2/StxB1 toxoid | Stx2 | 10/10 |
| E | StxA2/StxB1 toxoid | Stx1 and Stx2 | 9/10 |

Example 6

Determination of Anti-Stx1 or Anti-Stx2 Antibodies by ELISA

Male CD-1 mice were immunized and boosted at three-week intervals with either PBS or the triple-mutant toxoid. After the third and final boost, serum from each mouse was collected, and the titers of IgG antibodies against Stx1 and Stx2 were compared to the appropriate pre-immune serum sample by ELISA (see FIG. 2).

Purified Stx1 or Stx2 (100 ng in 100 ml PBS) was used to coat the wells of a U-bottom 96-well microtiter plate (Thermo Electron), and the microtiter plates were incubated at 4° C. overnight. The microtiter plates were then washed three times in PBS that contained 0.05% Tween-20 (PBST) and blocked overnight at 4° C. with 200 µl per well of PBST that contained 3% bovine serum albumin. The next day, in a separate microtiter plate, the mouse pre- and post-immunization sera were diluted in PBST, with an initial dilution of 1:50 and 1:5 dilutions thereafter. After the blocked microtiter plates were washed, 100 µl of the diluted serum was used as the primary antibody for the ELISAs, and the microtiter plates were incubated for two hours at 37° C. Next, 100 µl of the secondary antibody, goat anti-mouse IgG conjugated to HRP was added at a dilution of 1:3,000 in PBST, and the plates were incubated at room temperature for 45 min. The secondary antibody was detected with the TMB Peroxidase EIA substrate kit (Bio-Rad), and the microtiter plates were incubated at room temperature for 15 minutes to allow for a color change to develop. One hundred µl of 1M $H_2SO_4$ was then added to quench the reaction, and the color development was determined by measurement of the $OD_{450}$ The ELISA titer was defined as the serum dilution that was above both background and pre-immune levels. In cases where the pre-immune levels were higher than the post-immune levels, a value of 0.3 was assigned as the ELISA titer. These assays were done once in duplicate. The positive controls for the anti-Stx1 and anti-Stx2 ELISAs were either purified 11E10 or 13C4 (Hycult Biotechnology) as the primary antibodies, each diluted 1:20,000 in PBST.

Example 7

In vitro Stx1 and Stx2 Toxin Neutralization Assays

Because toxin neutralization titers are more predictive of a protective response to Stxs than ELISA titers (Wen et al., supra), in vitro Vero cell neutralization assays against purified Stx1 or Stx2 were also performed on serum samples.

The pre- and post-immunization sera were used in a neutralization assay for Stx1 and Stx2 as reported previously (Marques et al. (1986) J. Infect. Dis. 154, 338-41). The neutralization titer was defined as the dilution of the mouse serum that neutralized 50% of the cytotoxicity of Stx1 or Stx2. The amount of Stx1 or Stx2 used in these assays was 20 or 38 $CD_{50}$s respectively. In cases where the mock-immunized mouse serum or post-immunization serum did not neutralize either Stx1 or Stx2, a value of 0.3 was assigned to the neutralization titer. These assays were done once in duplicate.

Example 8

Comparison of Neutralization Antibody Titers Via Statistical Analysis

The anti-Stx1 or anti-Stx2 ELISA and in vitro neutralization antibody titers from the toxoid-immunized groups were compared to the mock-immunized groups by the two-sided t test using the program SPSS 12.0.1. The survival of immunized mice was compared to the mock-immunized mice after challenging with 10 LD50s of either Stx1 or Stx2 or Stx1 and Stx2 by the Fisher's exact test. These results were considered significantly different if the p value was <0.05.

Figure 2:
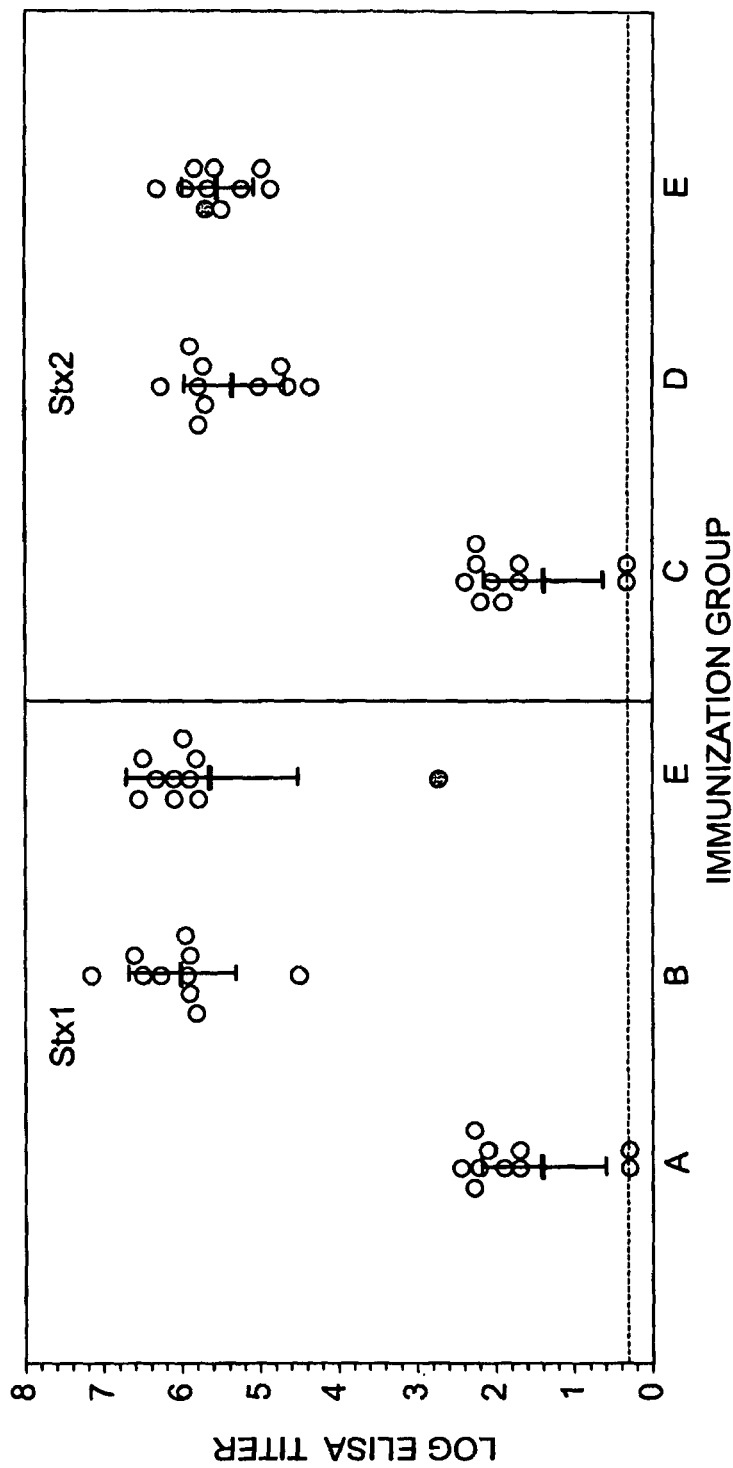
FIG. 2: Detection of anti-Stx1 or anti-Stx2 antibodies by ELISA. Serum IgG titers to Stx1 (left) or Stx2 (right) from mice immunized with either PBS (groups A and C) or the StxA2/StxB1 toxoid (groups B, D and E) are shown in FIG. 2. The horizontal bars represent the geometric mean of the log of the IgG serum titer to Stx1 or Stx2 and the error bars indicate ± one standard deviation. The shaded circles in groups E represent the mouse that died when challenged with Stx1 and Stx2. The dashed line represents the limit of detection.

The pre-immune and mock-immunized mice had low background levels of antibodies that reacted with Stx1 or Stx2 (see FIG. 2). All but one mouse immunized with the toxoid displayed high IgG titers to both Stx1 and Stx2, 4.4 and 4.1 logs above background, respectively. When the ELISA titers of the toxoid-immunized mice were compared to the mock-immunized mice, the results were found to be significant (p<0.001).

Figure 3:
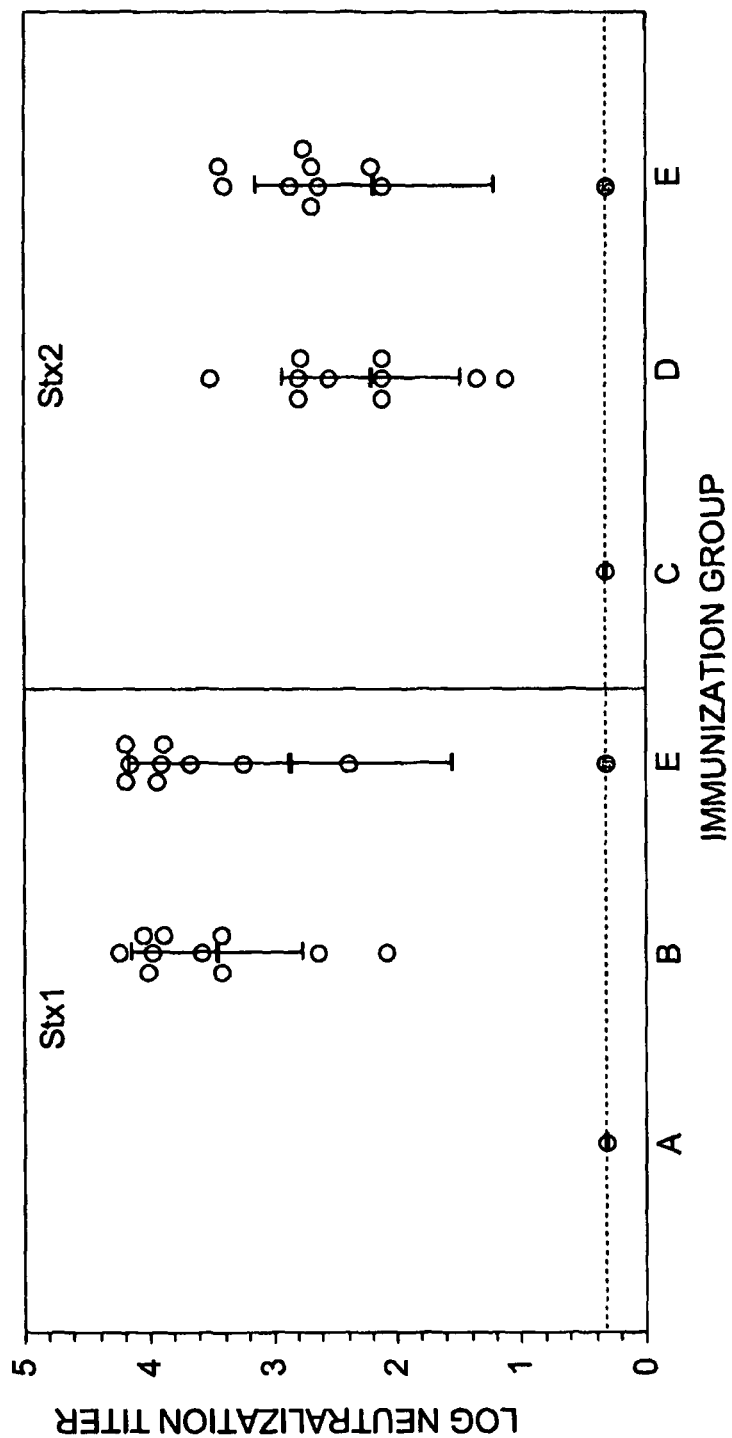
FIG. 3: In vitro Stx1 and Stx2 toxin neutralization assays. In vitro neutralization titers to Stx1 (left) and Stx2 (right) with antisera from mice immunized with either PBS (groups A and C) or the StxA2/StxB1 toxoid (groups B, D, and E) are shown in FIG. 3. The horizontal bars represent the geometric mean of the log of the neutralization titer to Stx1 or Stx2, and the error bars indicate ± one standard deviation. The amount of Stx1 and Stx2 used was 20 and 38 50% cytotoxic doses ($CD_{50}$), respectively. The shaded circle in groups E represents the mouse that died when challenged with Stx1 and Stx2. The dashed line represents the limit of detection.

No measurable neutralizing antibodies to either Stx1 or Stx2 were detected in pre-immune or mock-immunized mice (see FIG. 3). In contrast, all but one mouse immunized with the toxoid displayed neutralizing titers to Stx1 and Stx2 (see FIG. 3). The mean anti-Stx1 and anti-Stx2 neutralization titers were 2.9 and 1.9 logs above background. The lower Stx2-neutralizing titers may be attributable to the higher concentration of Stx2 than Stx1 used in the neutralization assays (about 38 $CD_{50}$s compared to 20 $CD_{50}$s, respectively). The toxoid-immunized mouse that showed a poor anti-Stx1 ELISA titer also failed to produce neutralizing antibodies against either toxin. When the neutralization titers of the toxoid-immunized mice were compared to the mock-immunized mice, the results were found to be significantly different (p<0.001).

Although the present invention has been described in detail, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. A chimeric protein selected from the group consisting of:
   (i) a chimeric protein comprising SEQ ID NO: 2,
   (ii) a chimeric protein encoded by the nucleic acid sequence of SEQ ID NO: 1, and
   (iii) a chimeric protein comprising SEQ ID NO: 2 and SEQ ID NO: 3.

2. A method of generating antibodies capable of binding to Stx comprising administering a chimeric protein of claim 1 to a mammal.

3. The method of claim 2, wherein the mammal is a human.

4. The method of claim 3, wherein the human is suffering from diarrhea.

5. The method of claim 3, wherein the human is suffering from hemolytic uremic syndrome.

6. A method of preventing hemolytic uremic syndrome in a mammal comprising administering a composition comprising the chimeric protein of claim 1.

7. A method of preventing diarrhea associated with Shiga toxin-producing *Escherichia coli* infection in a mammal comprising administering a composition comprising the chimeric protein of claim 1.

8. The chimeric protein of claim 1, wherein the chimeric protein is capable of inducing the production of broadly cross-reactive species of antibodies against shiga-like toxin 1 (Stx1) and shiga-like toxin 2 (Stx2) following immunization.

9. A composition comprising the chimeric protein of claim 1.

10. The composition of claim 9, further comprising a pharmaceutically acceptable carrier.

11. The composition of claim 9, further comprising an adjuvant.

12. The composition of claim 9, wherein said composition is suitable for administration to a human.

* * * * *